(12) United States Patent
Allio et al.

(10) Patent No.: US 10,149,822 B2
(45) Date of Patent: *Dec. 11, 2018

(54) COMPOSITIONS AND METHODS FOR COMBINATION INGREDIENT DELIVERY

(71) Applicant: The FIX, LLC, Providence, RI (US)

(72) Inventors: Michael K. Allio, Providence, RI (US); Stephen Lane, Providence, RI (US); Marco Wo, Providence, RI (US)

(73) Assignee: THE FIX, LLC, Prvidence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,583

(22) Filed: Oct. 7, 2016

(65) Prior Publication Data
US 2017/0020811 A1 Jan. 26, 2017

Related U.S. Application Data

(63) Continuation of application No. 15/159,433, filed on May 19, 2016, now Pat. No. 9,498,435, which is a
(Continued)

(51) Int. Cl.
*A61K 31/135* (2006.01)
*A61K 31/29* (2006.01)
(Continued)

(52) U.S. Cl.
CPC ............ *A61K 9/0056* (2013.01); *A23G 3/563* (2013.01); *A23L 2/52* (2013.01); *A61K 9/0095* (2013.01);
(Continued)

(58) Field of Classification Search
None
See application file for complete search history.

(56) References Cited

U.S. PATENT DOCUMENTS

| 5,244,670 A | 9/1993 | Upson et al. |
| 5,248,505 A * | 9/1993 | Garwin .................. A61K 31/80 424/472 |

(Continued)

FOREIGN PATENT DOCUMENTS

WO  WO-2016130830 A1  8/2016

OTHER PUBLICATIONS

PCT/US2016/017587 International Search Report and Written Opinion dated Apr. 14, 2016.
(Continued)

*Primary Examiner* — Ernst V Arnold
*Assistant Examiner* — Kyung S Chang
(74) *Attorney, Agent, or Firm* — Wilson Sonsini Goodrich & Rosati

(57) ABSTRACT

Described herein are compositions, methods, and devices for relief of a cough, cold, sore throat, or allergy, or a related symptom. Also described herein are compositions, methods, and devices for the prevention, treatment and/or amelioration of a digestive illness or digestive discomfort, or a related symptom of either. Such compositions may be in the form of a liquid composition and include a plurality of pharmaceutical ingredients and a plurality of botanical ingredients.

20 Claims, 5 Drawing Sheets

Related U.S. Application Data continuation of application No. PCT/US2016/017587, filed on Feb. 11, 2016.

(60) Provisional application No. 62/131,710, filed on Mar. 11, 2015, provisional application No. 62/115,069, filed on Feb. 11, 2015.

(51) Int. Cl.

| | |
|---|---|
| *A61K 31/695* | (2006.01) |
| *A61K 33/10* | (2006.01) |
| *A61K 9/00* | (2006.01) |
| *A61K 31/616* | (2006.01) |
| *A23G 3/56* | (2006.01) |
| *A23L 2/52* | (2006.01) |
| *A61K 31/045* | (2006.01) |
| *A61K 31/047* | (2006.01) |
| *A61K 31/09* | (2006.01) |
| *A61K 31/137* | (2006.01) |
| *A61K 31/19* | (2006.01) |
| *A61K 31/194* | (2006.01) |
| *A61K 31/245* | (2006.01) |
| *A61K 31/7028* | (2006.01) |
| *A61K 35/644* | (2015.01) |
| *A61K 36/185* | (2006.01) |
| *A61K 36/28* | (2006.01) |
| *A61K 36/53* | (2006.01) |
| *A61K 36/59* | (2006.01) |
| *A61K 36/73* | (2006.01) |
| *A61K 36/752* | (2006.01) |
| *A61K 36/899* | (2006.01) |
| *A61K 36/9066* | (2006.01) |
| *A61K 36/9068* | (2006.01) |
| *A61K 31/05* | (2006.01) |
| *A61K 31/167* | (2006.01) |
| *A61K 31/192* | (2006.01) |
| *A61K 31/4402* | (2006.01) |
| *A61K 31/4453* | (2006.01) |
| *A61K 31/485* | (2006.01) |
| *A61K 31/522* | (2006.01) |
| *A61K 31/7004* | (2006.01) |
| *A61K 31/80* | (2006.01) |
| *A61K 47/46* | (2006.01) |

(52) U.S. Cl.
CPC .......... *A61K 31/045* (2013.01); *A61K 31/047* (2013.01); *A61K 31/05* (2013.01); *A61K 31/09* (2013.01); *A61K 31/135* (2013.01); *A61K 31/137* (2013.01); *A61K 31/167* (2013.01); *A61K 31/19* (2013.01); *A61K 31/192* (2013.01); *A61K 31/194* (2013.01); *A61K 31/245* (2013.01); *A61K 31/29* (2013.01); *A61K 31/4402* (2013.01); *A61K 31/4453* (2013.01); *A61K 31/485* (2013.01); *A61K 31/522* (2013.01); *A61K 31/616* (2013.01); *A61K 31/695* (2013.01); *A61K 31/7004* (2013.01); *A61K 31/7028* (2013.01); *A61K 31/80* (2013.01); *A61K 33/10* (2013.01); *A61K 35/644* (2013.01); *A61K 36/185* (2013.01); *A61K 36/28* (2013.01); *A61K 36/53* (2013.01); *A61K 36/59* (2013.01); *A61K 36/73* (2013.01); *A61K 36/752* (2013.01); *A61K 36/899* (2013.01); *A61K 36/9066* (2013.01); *A61K 36/9068* (2013.01); *A61K 47/46* (2013.01); *A23V 2002/00* (2013.01)

(56) References Cited

U.S. PATENT DOCUMENTS

| | | |
|---|---|---|
| 5,498,426 A | 3/1996 | Wilson et al. |
| 5,922,347 A | 7/1999 | Hausler et al. |
| 6,491,540 B1 | 12/2002 | Barreca |
| 6,576,267 B2 | 6/2003 | Gelber et al. |
| 6,602,518 B2 | 8/2003 | Seielstad et al. |
| 6,613,346 B2 | 9/2003 | Seielstad et al. |
| 6,652,839 B2 | 11/2003 | Barreca |
| 6,759,062 B2 | 7/2004 | Gelber et al. |
| 6,787,164 B2 | 9/2004 | Gelber et al. |
| 6,793,942 B2 | 9/2004 | Gelber et al. |
| 6,814,958 B1 | 11/2004 | Sekimoto |
| 6,841,544 B2 | 1/2005 | Gelber et al. |
| 6,869,614 B2 | 3/2005 | Barreca |
| 7,351,425 B2 | 4/2008 | Barreca |
| 7,585,890 B2 | 9/2009 | Berg et al. |
| 7,671,086 B2 | 3/2010 | Berg |
| 7,678,768 B2 | 3/2010 | Purpura et al. |
| 7,955,632 B2 | 6/2011 | Paulsen et al. |
| 8,114,455 B2 | 2/2012 | Paulsen et al. |
| 8,293,265 B2 | 10/2012 | Paulsen et al. |
| 8,361,519 B2 | 1/2013 | Levine et al. |
| 8,512,787 B2 | 8/2013 | Paulsen et al. |
| 8,591,962 B2 | 11/2013 | Ma et al. |
| 8,623,426 B2 | 1/2014 | Ma et al. |
| 8,679,522 B2 | 3/2014 | Barreca |
| 8,679,553 B2 | 3/2014 | Levine et al. |
| 8,865,240 B2 | 10/2014 | Paulsen et al. |
| 9,253,991 B2 | 2/2016 | Barreca |
| 9,498,435 B2 | 11/2016 | Allio et al. |
| 2006/0073189 A1 | 4/2006 | Pinney et al. |
| 2006/0205752 A1 | 9/2006 | Whitehead |
| 2009/0274662 A1* | 11/2009 | Magowan ............ A61K 31/606 424/93.4 |
| 2011/0206721 A1* | 8/2011 | Nair ....................... A61K 36/06 424/195.15 |
| 2012/0189560 A1 | 7/2012 | Idlibi |
| 2012/0225100 A1 | 9/2012 | Darcy et al. |
| 2014/0294915 A1 | 10/2014 | Barreca et al. |
| 2015/0224052 A1 | 8/2015 | Paulsen et al. |
| 2016/0256383 A1 | 9/2016 | Allio et al. |

OTHER PUBLICATIONS

U.S. Appl. No. 15/159,433 Notice of Allowance dated Sep. 13, 2016.
PCT/US2016/017587 International Preliminary Report on Patentability dated Aug. 24, 2017.

* cited by examiner

COMPOSITIONS AND METHODS FOR COMBINATION INGREDIENT DELIVERY

CROSS-REFERENCE

This application is a continuation of U.S. patent application Ser. No. 15/159,433 filed May 19, 2016, which is a continuation of PCT Patent Application No. PCT/US2016/17587 filed on Feb. 11, 2016, which claims the benefit of U.S. Provisional Application No. 62/115,069 filed Feb. 11, 2015, and U.S. Provisional Application No. 62/131,710 filed Mar. 11, 2015, each of which is incorporated herein its entirety.

BACKGROUND

It is known that the common cold is not a single entity, but rather is a group of diseases caused by members of several families of viruses. In addition, a sore throat is a common disease state which is both associated with colds, related illnesses and allergies with similar symptoms. There exists a need to enhance the performance of clinically proven medications to provide more effective prevention, treatment or amelioration of a cold, cough, sore throat, allergy or related symptoms in individuals. There also exists a need to enhance the performance of clinically proven medications and also provide a more soothing and/or better tasting form of relief.

Digestive illnesses and related symptoms can arise from acute or chronic conditions in individuals. There exists a need to enhance the performance of clinically proven medications to provide more effective prevention, treatment or amelioration of digestive discomfort in individuals. There exists a need to enhance the performance of clinically proven medications and also provide a more soothing and/or better tasting form of relief.

BRIEF SUMMARY

Methods, compositions, devices and systems are described herein for the prevention, amelioration, and/or treatment of a cough, cold, sore throat, or allergy or a related symptom. Also described herein methods, compositions, devices and systems for the prevention, amelioration, and/or treatment a digestive illness or digestive discomfort, or a related symptom. Combination products for providing such relief which include a plurality of active pharmaceutical ingredients and a plurality of botanical ingredients.

Provided herein are compositions comprising a plurality of active pharmaceutical ingredients, wherein the plurality of pharmaceutical ingredients comprises an analgesic, anesthetic, antihistamine, antitussive, expectorant, decongestant, or demulcent, and wherein each of the active pharmaceutical ingredients provides relief for a cold, cough, or a sore throat, or a related symptom; and a plurality of botanical ingredients, wherein the plurality of active pharmaceutical ingredients and the plurality of botanical ingredients are present in a ratio by weight of about 1:32 to 1:65. Further provided herein are compositions wherein the plurality of active pharmaceutical ingredients and the plurality of botanical ingredients are present in a ratio by weight of about 1:64. Further provided herein are compositions wherein the plurality of active pharmaceutical ingredients and the plurality of botanical ingredients are present in a ratio by weight of 1:64. Further provided herein are compositions wherein the analgesic is acetaminophen, ibuprofen, aspirin or naproxen. Further provided herein are compositions wherein the anesthetic is benzocaine, lidocaine, dyclonine, or hexylresorcinol. Further provided herein are compositions wherein the antihistamine is brompheniramine, chlorpheniramine, diphenhydramine, or dimenhydrinate. Further provided herein are compositions wherein the expectorant is guaifenesin. Further provided herein are compositions wherein the decongestant is phenylephrine or pseudoephedrine. Further provided herein are compositions wherein the demulcent is glycerin. Further provided herein are compositions wherein the antitussive is menthol. Further provided herein are compositions wherein the composition comprises at least three active pharmaceutical ingredients, each of which are an analgesic, antitussive, or anesthetic. Further provided herein are compositions wherein the at least three active pharmaceutical ingredients comprise: aspirin, naproxen, ibuprofen, acetaminophen, menthol, benzocaine, lidocaine, dyclonine, hexylresorcinol, or ketoprofen. Further provided herein are compositions wherein the at least three active pharmaceutical ingredients are aspirin, menthol, and benzocaine. Further provided herein are compositions wherein the at least three active pharmaceutical ingredients comprise acetaminophen, menthol, and benzocaine. Further provided herein are compositions wherein the plurality of botanical ingredients comprises thyme, Echinacea, horehound, ginger, mint, propolis, white willow bark, cayenne, sage, marshmallow powder, turmeric (curcumin), andographis, pelargonium sidoides, cinnamon powder, lavender, goldenseal, spilanthes, elderberry, barberry, licorice, slippery elm, pectin, glycerin, chamomile, honey, isomalt, tartaric acid, lemon oil, tinofend, stevia, or astragalus. Further provided herein are compositions wherein the plurality of botanical ingredients comprises at thyme, Echinacea, marshmallow powder, elderberry, honey, isomalt, tartaric acid, lemon oil, tinofend, and stevia. Further provided herein are compositions wherein the plurality of botanical ingredients comprises a botanical ingredient with an immune-boosting, soothing, lubricating, antimicrobial, antibacterial, pain relief, or anti-inflammatory property. Further provided herein are compositions wherein the plurality of botanical ingredients enhances the flavor profile of the composition. Further provided herein are compositions wherein the plurality of botanical ingredients enhances an activity of at least one of the active pharmaceutical ingredients. Further provided herein are compositions wherein the plurality of botanical ingredients has a synergistic effect with at least one of the active pharmaceutical ingredients. Further provided herein are compositions wherein the plurality of botanical ingredients enhances an immune system response against a virus associated with the cold, cough or sore throat. Further provided herein are compositions wherein the virus is parainfluenza virus, rhinovirus, respiratory syncytial virus, enteroviruses, picornavirus, and coronavirus, metapneumovirus, or adenovirus. Further provided herein are compositions wherein the plurality of botanical ingredients enhances the activity of at least one of the active pharmaceutical ingredients to provide relief for coughing, pain, chest congestion, nasal congestion, fever, runny nose, muscle ache, fatigue, loss of appetite, or headache. Further provided herein are compositions wherein the composition is in the form of a lollipop, lozenge, powder, or liquid. Further provided herein are methods for providing relief for a cold, cough, sore throat, or a related symptom, comprising administering to a subject in need thereof a composition described herein. Further provided herein are methods comprising administering an effective amount of the plurality of active pharmaceutical ingredients to provide relief for a cold, cough, sore throat, or a related symptom. Further provided here are devices for cold, cough, or sore throat relief, comprising: a) a first region, wherein the first region has a form that complements the interior of a mouth, and wherein the first region comprises a composition described herein; and b) a second region, wherein the second region is in the shape of a handle and extends into the first region. Further provided herein are devices wherein the first region comprises an inner layer and an outer layer, and wherein the handle extends through the outer layer and into the inner layer.

Provided herein are compositions comprising a plurality of active pharmaceutical ingredients, wherein the plurality of active pharmaceutical ingredients comprises an analgesic, antihistamine, antitussive, expectorant, nasal decongestant, or demulcent, and wherein the plurality of active pharmaceutical ingredients is present in an amount of about 80 to 700 mg, and wherein the plurality of active pharmaceutical ingredients provides relief for a cold, cough, or sore throat, or a related symptom; and a plurality of botanical ingredients, and wherein the plurality of botanical ingredients is present in an amount of about 5000 to 22000 mg. Further provided herein are compositions wherein the plurality of active pharmaceutical ingredients is present in an amount of about 335 or 85 mg. Further provided herein are compositions wherein the plurality of botanical ingredients is present in an amount of about 22000 or 5400 mg. Further provided herein are compositions wherein the analgesic acetaminophen, ibuprofen, aspirin or naproxen. Further provided herein are compositions wherein the anesthetic is benzocaine, lidocaine, dyclonine, or hexylresorcinol. Further provided herein are compositions wherein the antihistamine is brompheniramine, chlorpheniramine, diphenhydramine, or dimenhydrinate. Further provided herein are compositions wherein the antitussive is menthol. Further provided herein are compositions wherein the expectorant is guaifenesin. Further provided herein are compositions wherein the decongestant is phenylephrine or pseudoephedrine. Further provided herein are compositions wherein the demulcent is glycerin. Further provided herein are compositions wherein the composition comprises at least three active pharmaceutical ingredients, each of which are an analgesic, antitussive, or anesthetic. Further provided herein are compositions wherein the at least three active pharmaceutical ingredients comprise: aspirin, naproxen, ibuprofen, acetaminophen, menthol, benzocaine, lidocaine, dyclonine, hexylresorcinol, or ketoprofen. Further provided herein are compositions wherein the at least three active pharmaceutical ingredients comprise aspirin, menthol, or benzocaine. Further provided herein are compositions wherein the plurality of botanical ingredients comprises thyme, Echinacea, horehound, ginger, mint, propolis, white willow bark, cayenne, sage, marshmallow powder, turmeric (curcumin), andographis, pelargonium sidoides, cinnamon powder, lavender, goldenseal, spilanthes, elderberry, barberry, licorice, slippery elm, pectin, glycerin, chamomile, honey, isomalt, tartaric acid, lemon oil, tinofend, stevia, or astragalus. Further provided herein are compositions wherein the plurality of botanical ingredients comprises thyme, Echinacea, marshmallow powder, elderberry, honey, isomalt, tartaric acid, lemon oil, tinofend, and stevia. Further provided herein are compositions wherein the plurality of botanical ingredients comprises a botanical ingredient with an immune-boosting, soothing, lubricating, antimicrobial, antibacterial, pain relief, or anti-inflammatory property. Further provided herein are compositions wherein the plurality of botanical ingredients enhances the flavor profile of the composition. Further provided herein are compositions wherein the plurality of botanical ingredients enhances an activity of at least one of the active pharmaceutical ingredients. Further provided herein are compositions wherein the plurality of botanical ingredients has a synergistic effect with at least one of the active pharmaceutical ingredients. Further provided herein are compositions wherein the plurality of botanical ingredients enhances an immune system response against a virus associated with the cold, cough or sore throat. Further provided herein are compositions wherein the virus is parainfluenza virus, rhinovirus, respiratory syncytial virus, enteroviruses, picornavirus, and coronavirus, metapneumovirus, or adenovirus. Further provided herein are compositions wherein the plurality of botanical ingredients enhances the activity of at least one of the active pharmaceutical ingredients to provide relief for coughing, pain, chest congestion, nasal congestion, fever, runny nose, muscle ache, fatigue, loss of appetite, or headache. Further provided herein are compositions wherein the composition is in the form of a lollipop, lozenge, powder, or liquid. Further provided herein are compositions wherein the composition comprises: a) aspirin or acetaminophen present in an amount of about 325 to 650 mg; b) menthol present in an amount of about 5 to 10 mg; c)benzocaine present in an amount about 2 to 15 mg; d) cooked isomalt present in an amount of about 18000 to 21000 mg; e) elderberry tincture present in an amount of about 1000 to 1200 mg; f) honey present in an amount of about 400 to 600 mg; g) tartaric acid present in an amount of about 30 to 60 mg; h) marshmallow powder present in an amount of about 30 to 60 mg; i) lemon oil present in an amount of about 10 to 30 mg; j) Echinacea extract present in an amount of about 8 to 16 mg; k) tinofend present in an amount of about 5 to 15 mg; l) Stevia, 40% present in an amount of about 5 to 15 mg; and m) Thyme oil present in an amount of about 1 to 10 mg. Further provided herein are compositions wherein the composition comprises: a) aspirin present in an amount of about 70 to 90 mg; b) menthol present in an amount of about 0.5 to 3 mg; c) benzocaine present in an amount about 0.5 to 3 mg; d) cooked isomalt present in an amount of about 4000 to 6000 mg; e) elderberry tincture present in an amount of about 200 to 400 mg; f) honey present in an amount of about 50 to 300 mg; g) tartaric acid present in an amount of about 5 to 20 mg; h) marshmallow powder present in an amount of about 5 to 20 mg; i) lemon oil present in an amount of about 1 to 10 mg; j) Echinacea extract present in an amount of about 1 to 10 mg; k) tinofend present in an amount of about 0.5 to 5 mg; l) Stevia, 40% present in an amount of about 0.5 to 5 mg; and m) Thyme oil present in an amount of about 0.5 to 5 mg. Further provided herein are compositions wherein the composition is in the form of a lollipop, lozenge, powder, or liquid. Further provided herein are methods for providing relief for a cold, cough, sore throat, or a related symptom, comprising administering to a subject in need thereof a composition described herein. Further provided herein are methods comprising administering an effective amount of the plurality of active pharmaceutical ingredients to provide relief for a cold, cough, sore throat, or a related symptom. Further provided here are devices for cold, cough, or sore throat relief, comprising: a) a first region, wherein the first region has a form that complements the interior of a mouth, and wherein the first region comprises a composition described herein; and b) a second region, wherein the second region is in the shape of a handle and extends into the first region. Further provided herein are devices wherein the first region comprises an inner layer and an outer layer, and wherein the handle extends through the outer layer and into the inner layer.

Provided herein are compositions for cold, cough, or sore throat relief, wherein the compositions are in the form of a lollipop and comprises: a) aspirin present in an amount of about 325 to 650 mg; b) menthol present in an amount of about 5 to 10 mg; c) benzocaine present in an amount about 2 to 15 mg; d) cooked isomalt present in an amount of about 19974 mg; e) elderberry tincture present in an amount of about 1100 mg; f) honey present in an amount of about 440 mg; g) tartaric acid present in an amount of about 55 mg; h) marshmallow powder present in an amount of about 40 mg; i) lemon oil present in an amount of about 20 mg; j) Echinacea extract present in an amount of about 12 mg; k) tinofend present in an amount of about 10 mg; l) Stevia, 40% present in an amount of about 9 mg; and m) Thyme oil present in an amount of about 4 mg. Further provided herein are methods for providing relief for a cold, cough, sore throat, or a related symptom, comprising administering to a subject in need thereof a compositions described herein. Further provided herein are methods comprising administering an effective amount of the plurality of active pharmaceutical ingredients to provide relief for a cold, cough, sore throat, or a related symptom. Further provided here are devices for cold, cough, or sore throat relief, comprising: a) a first region, wherein the first region has a form that complements the interior of a mouth, and wherein the first region comprises a composition described herein; and b) a second region, wherein the second region is in the shape of a handle and extends into the first region. Further provided herein are devices wherein the first region comprises an inner layer and an outer layer, and wherein the handle extends through the outer layer and into the inner layer.

Provided herein are compositions for cold, cough, or sore throat relief, wherein the compositions are in the form of a lozenge and comprises: a) aspirin present in an amount of about 81.25 mg; b) menthol present in an amount of about 1.5 mg; c) benzocaine present in an amount about 1.25 mg; d) cooked isomalt present in an amount of about 4993.5 mg; e) elderberry tincture present in an amount of about 275 mg; f) honey present in an amount of about 110 mg; g) tartaric acid present in an amount of about 13.75 mg; h) marshmallow powder present in an amount of about 10 mg; i) lemon oil present in an amount of about 5 mg; j) Echinacea extract present in an amount of about 3 mg; k) tinofend present in an amount of about 2.5 mg; l) Stevia, 40% present in an amount of about 2.25 mg; and m) Thyme oil present in an amount of about 1 mg. Further provided herein are methods for providing relief for a cold, cough, sore throat, or a related symptom, comprising administering to a subject in need thereof a composition described herein. Further provided herein are methods comprising administering an effective amount of the plurality of active pharmaceutical ingredients to provide relief for a cold, cough, sore throat, or a related symptom. Further provided here are devices for cold, cough, or sore throat relief, comprising: a) a first region, wherein the first region has a form that complements the interior of a mouth, and wherein the first region comprises a composition described herein; and b) a second region, wherein the second region is in the shape of a handle and extends into the first region. Further provided herein are devices wherein the first region comprises an inner layer and an outer layer, and wherein the handle extends through the outer layer and into the inner layer.

Provided herein are compositions for sore throat relief, comprising a plurality of active pharmaceutical ingredients, wherein the plurality of active pharmaceutical ingredients comprises an analgesic, antihistamine, antitussive, expectorant, nasal decongestant, or demulcent; and a plurality of botanical ingredients, wherein the plurality of botanical ingredients comprises cooked isomalt, elderberry tincture, honey, tartaric acid, marshmallow powder, lemon oil, Echinacea extract, tinofend stevia, and thyme oil, wherein the one or more active pharmaceutical ingredients and the plurality of botanical ingredients are present in a ratio by weight of about 1:32 to 1:65. Further provided herein are compositions wherein the plurality of pharmaceutical ingredients and the plurality of botanical ingredients are present in a ratio by weight of about 1:64. Further provided herein are compositions wherein the plurality of active pharmaceutical ingredients and the plurality of botanical ingredients are present in a ratio by weight of 1:64. Further provided herein are compositions wherein the composition comprises multiple layers. Further provided herein are compositions wherein the multiple layers comprise: a) an inner layer; wherein the inner layer is solid, semi-solid, gelatinous, or liquid; and b) an outer layer, wherein the outer layer is solid, semi-solid or gelatinous. Further provided herein are compositions wherein the outer layer is a shape and size such that it has a form that complements the interior of a mouth. Further provided herein are compositions wherein the inner layer comprises the plurality of botanical ingredients and the outer layer comprises the plurality of pharmaceutical ingredients. Further provided herein are compositions wherein the outer layer comprises the plurality of botanical ingredients and the inner layer comprises the plurality of pharmaceutical ingredients. Further provided herein are compositions wherein the inner layer and the outer layer are separated in a patterned form. Further provided herein are compositions wherein the composition comprises multiple matrices, wherein each matric comprises a different group of ingredients. Further provided herein are methods for providing relief for a cold, cough, sore throat, or a related symptom, comprising administering to a subject in need thereof a composition described herein. Further provided herein are methods comprising administering an effective amount of the plurality of active pharmaceutical ingredients to provide relief for a cold, cough, sore throat, or a related symptom. Further provided here are devices for cold, cough, or sore throat relief, comprising: a) a first region, wherein the first region has a form that complements the interior of a mouth, and wherein the first region comprises a composition described provided herein; and b) a second region, wherein the second region is in the shape of a handle and extends into the first region. Further provided herein are devices wherein the first region comprises an inner layer and an outer layer, and wherein the handle extends through the outer layer and into the inner layer.

Provided herein are compositions comprising a plurality of active pharmaceutical ingredients, wherein the plurality of pharmaceutical ingredient comprises an antacid, antidiarrheal, antiemetic, antiflatulent, stomach acidifier, or overindulgence reliever, and wherein the plurality of active pharmaceutical ingredient provides for prevention, amelioration or treatment of a disease state associated with a digestive illness; and a plurality of botanical ingredients, wherein the plurality of active pharmaceutical ingredients and the plurality of botanical ingredients are present in a ratio by weight of about 1:5 to 1:11. Further provided herein are compositions wherein the plurality of active pharmaceutical ingredients and the plurality of botanical ingredients are present in a ratio by weight of about 1:7.5. Further provided herein are compositions wherein the plurality of active pharmaceutical ingredients and the plurality of botanical ingredients are present in a ratio by weight of 1:7.5. Further provided herein are compositions wherein the antacid is calcium carbonate or bismuth subsalicylate. Further provided herein are compositions wherein the antidiarrheal is alumina powder, bismuth subsalicylate, calcium gluconate, calcium polycarbophil, carboxymethylcellulose sodium, charcoal, glycine, homatropine methylbromide, hyocyamine sulfate, kaolin, *lactobacillus acidophilis, lactobacillus bulgaricus*, loperamine HCl, opium powder, opium tincture, paregoric, pectin, phenyl salicylate, psyllium husk, polycarbophil, potassium carbonate, scopolamine hydrobromide, sodium carboxymethylcellulose, or zinc phenolsulfonate. Further provided herein are compositions wherein the antiemetic is dimenhydrinate or meclizine hydrochloride. Further provided herein are compositions wherein the antiflatulent is simethicone. Further provided herein are compositions wherein the stomach acidifier is glutamic acid hydrochloride. Further provided herein are compositions wherein the overindulgence reliever is acetaminophen, aluminum hydroxide, aluminum hydroxide gel, aspirin, bismuth subsalicylate, caffeine, fructose, magnesium carbonate, magnesium trisilicate, sodium citrate in solution, or sodium acetylsalicylate. Further provided herein are compositions wherein the plurality of active pharmaceutical ingredients comprises an antacid and an antiflatulent. Further provided herein are compositions wherein the plurality of active pharmaceutical ingredients comprises calcium carbonate and simethicone. Further provided herein are compositions wherein the plurality of active pharmaceutical ingredients comprises bismuth subsalicylate and simethicone. Further provided herein are compositions wherein the plurality of botanical ingredients comprises honey, oats, catnip glycerin, chamomile flowers, marshmallow powder, meadowsweet, ginger powder, or turmeric. Further provided herein are compositions wherein the plurality of botanical ingredients comprises honey, oats, catnip glycerin, chamomile, marshmallow powder, meadowsweet, ginger powder and turmeric. Further provided herein are compositions wherein the plurality of botanical ingredients comprises honey, chamomile, meadowsweet, ginger powder, turmeric, or lemon balm. Further provided herein are compositions wherein the plurality of botanical ingredients comprises honey, chamomile, meadowsweet, ginger powder, turmeric, and lemon balm. Further provided herein are compositions wherein the plurality of active pharmaceutical ingredients and the plurality of botanical ingredients are located within a liquid, slurry, or gelatinous medium. Further provided herein are compositions further comprising a microstructure which comprises the plurality of active pharmaceutical ingredients. Further provided herein are compositions further comprising a microstructure which comprises the plurality of botanical ingredients. Further provided herein are compositions further comprising a barrier which separates a region from direct communication with the liquid, slurry, or gelatinous medium. Further provided herein are compositions wherein the barrier is removable by application of pressure, temperature, or enzymatic reaction. Further provided herein are compositions wherein the separated region comprises the plurality of active pharmaceutical ingredients or the plurality of botanical ingredients. Further provided herein are compositions wherein the liquid is carbonated or creamy. Further provided herein are compositions wherein the plurality of botanical ingredients comprises a botanical ingredient with an immune-boosting, soothing, lubricating, antimicrobial, antibacterial, pain relief, or anti-inflammatory property. Further provided herein are compositions wherein the plurality of botanical ingredients enhances an activity of at least one of the active pharmaceutical ingredients. Further provided herein are compositions wherein the plurality of botanical ingredients has a synergistic effect with at least one of the active pharmaceutical ingredients. Further provided herein are compositions wherein the plurality of botanical ingredients enhances an immune system response against a virus associated the digestive illness. Further provided herein are compositions wherein the virus is a norovirus, rotavirus, adenovirus, parvovirus or astrovirus. Further provided herein are compositions wherein the digestive illness is associated with a food allergy, food sensitivity, celiac disease, irritable bowel syndrome (IBS), overindulgence in food or alcohol, gastroesophageal reflux disease (GERD), ulcerative colitis, Crohn's disease, bacterial infection, parasitic infection or viral infection. Further provided herein are compositions wherein the plurality of botanical ingredients enhances the flavor profile of the composition. Further provided herein are methods for prevention, amelioration or treatment of a disease state associated with a digestive illness, comprising administering to a subject in need thereof a composition described herein. Further provided herein are methods further administering an effective amount of the plurality of active pharmaceutical ingredients to prevent, ameliorate or treat a disease state associated with a digestive illness. Further provided herein are devices for digestive relief, comprising: a) a mixture for digestive relief comprising: i) a composition described; and ii) a solution in fluid communication with the plurality of active pharmaceutical ingredients; and b) a container enclosing the mixture. Further provided herein are devices for digestive relief, comprising: a) a mixture for digestive relief comprising: i) a composition described; and ii) a solution in fluid communication with the plurality of botanical ingredients; and b) a container enclosing the mixture.

Provided herein are compositions comprising a plurality of active pharmaceutical ingredients, wherein the plurality of active pharmaceutical ingredients comprises an antacid, antidiarrheal, antiemetic, antiflatulent, stomach acidifier, or overindulgence reliever, and wherein the plurality of active pharmaceutical ingredients are present in an amount of about 1100 to 2200 mg, and wherein the plurality of active pharmaceutical ingredient provides for prevention, amelioration or treatment of a disease state associated with a digestive illness; and a plurality of botanical ingredients, and wherein the plurality of botanical ingredients is present in an amount of about 12000 to 13000 mg. Further provided herein are compositions wherein the plurality of active pharmaceutical ingredients is present in an amount of about 1625 mg. Further provided herein are compositions wherein the plurality of botanical ingredients is present in an amount of about 12255 or 12700 mg. Further provided herein are compositions wherein the antacid is calcium carbonate or bismuth subsalicylate. Further provided herein are compositions wherein the antidiarrheal is alumina powder, bismuth subsalicylate, calcium gluconate, calcium polycarbophil, carboxymethylcellulose sodium, charcoal, glycine, homatropine methylbromide, hyocyamine sulfate, kaolin, *lactobacillus acidophilis, lactobacillus bulgaricus*, loperamine HCl, opium powder, opium tincture, paregoric, pectin, phenyl salicylate, psyllium husk, polycarbophil, potassium carbonate, scopolamine hydrobromide, sodium carboxymethylcellulose, or zinc phenolsulfonate. Further provided herein are compositions wherein the antiemetic is dimenhydrinate or meclizine hydrochloride. Further provided herein are compositions wherein the antiflatulent is simethicone. Further provided herein are compositions wherein the stomach acidifier is glutamic acid hydrochloride. Further provided herein are compositions wherein the overindulgence reliever is acetaminophen, aluminum hydroxide, aluminum hydroxide gel, aspirin, bismuth subsalicylate, caffeine, fructose, magnesium carbonate, magnesium trisilicate, sodium citrate in solution, or sodium acetylsalicylate. Further provided herein are compositions wherein the plurality of active pharmaceutical ingredients comprises an antacid and an antiflatulent. Further provided herein are compositions wherein the plurality of active pharmaceutical ingredients comprises calcium carbonate and simethicone. Further provided herein are compositions wherein the plurality of active pharmaceutical ingredients comprises bismuth subsalicylate and simethicone. Further provided herein are compositions wherein the plurality of botanical ingredients comprises honey, oats, catnip glycerin, chamomile flowers, marshmallow powder, meadowsweet, ginger powder, or turmeric. Further provided herein are compositions wherein the plurality of botanical ingredients comprises honey, oats, catnip glycerin, chamomile, marshmallow powder, meadowsweet, ginger powder and turmeric. Further provided herein are compositions wherein the plurality of botanical ingredients comprises honey, chamomile, meadowsweet, ginger powder, turmeric, or lemon balm. Further provided herein are compositions wherein the plurality of botanical ingredients comprises honey, chamomile, meadowsweet, ginger powder, turmeric, and lemon balm. Further provided herein are compositions wherein the plurality of active pharmaceutical ingredients and the plurality of botanical ingredients are located within a liquid, slurry, or gelatinous medium. Further provided herein are compositions comprising a microstructure which comprises the plurality of active pharmaceutical ingredients. Further provided herein are compositions comprising a microstructure which comprises the plurality of botanical ingredients. Further provided herein are compositions comprising a barrier which separates a region from direct communication with the liquid, slurry, or gelatinous medium. Further provided herein are compositions wherein the barrier is removable by application of pressure, temperature, or enzymatic reaction. Further provided herein are compositions wherein the separated region comprises the plurality of active pharmaceutical ingredients or the plurality of botanical ingredients. Further provided herein are compositions wherein the liquid is carbonated or creamy. Further provided herein are compositions wherein the plurality of botanical ingredients comprises a botanical ingredient with an immune-boosting, soothing, lubricating, antimicrobial, antibacterial, pain relief, or anti-inflammatory property. Further provided herein are compositions wherein the plurality of botanical ingredients enhances an activity of at least one of the active pharmaceutical ingredients. Further provided herein are compositions wherein the plurality of botanical ingredients has a synergistic effect with at least one of the active pharmaceutical ingredients. Further provided herein are compositions wherein the plurality of botanical ingredients enhances an immune system response against a virus associated the digestive illness. Further provided herein are compositions wherein the virus is a norovirus, rotavirus, adenovirus, parvovirus or astrovirus. Further provided herein are compositions wherein the digestive illness is associated with a food allergy, food sensitivity, celiac disease, irritable bowel syndrome (IBS), overindulgence in food or alcohol, gastroesophageal reflux disease (GERD), ulcerative colitis, Crohn's disease, bacterial infection, parasitic infection or viral infection. Further provided herein are compositions wherein the plurality of botanical ingredients enhances the flavor profile of the composition. Further provided herein are compositions wherein the composition comprises: a) calcium carbonate present in an amount of about 1000 to 2000 mg; b) simethicone present in an amount of about 50 to 200 mg; c) honey present in an amount about 5000 to 6000 mg; d) oats present in an amount about 4000 to 5000 mg; e) catnip glycerine present in an amount of about 500 to 1000 mg; f) chamomile flower present in an amount of about 300 to 600 mg; g) marshmallow powder present in an amount of about 200 to 500 mg; h) meadowsweet present in an amount of about 200 to 500 mg; i) ginger powder present in an amount of about 100 to 300 mg; and j) turmeric present in an amount of about 50 to 150 mg. Further provided herein are compositions wherein the composition is in the form of a slurry. Further provided herein are compositions wherein the composition comprises: a) calcium carbonate present in an amount of about 1000 to 2000 mg; b) simethicone present in an amount of about 50 to 200 mg; c) honey present in an amount about 4000 to 5000 mg; d) meadowsweet present in an amount of about 2500 to 3500 mg; e) chamomile present in an amount of about 1500 to 2000 mg; f) lemon balm present in an amount of about 2000 to 3500 mg; and g) turmeric present in an amount of about 400 to 600 mg. Further provided herein are compositions wherein the composition is in the form of a tonic. Further provided herein are methods for prevention, amelioration or treatment of a disease state associated with a digestive illness, comprising administering to a subject in need thereof a composition described. Further provided herein are methods comprising administering an effective amount of the plurality of active pharmaceutical ingredients to prevent, ameliorate or treat a disease state associated with a digestive illness. Further provided herein are devices for digestive relief, comprising: a) a mixture for digestive relief comprising: i) a composition described; and ii) a solution in fluid communication with the plurality of active pharmaceutical ingredients; and b) a container enclosing the mixture. Further provided herein are devices for digestive relief, comprising: a) a mixture for digestive relief comprising: i) a composition described; and ii) a solution in fluid communication with the plurality of botanical ingredients; and b) a container enclosing the mixture.

Provided herein are compositions for digestive relief, comprising a plurality of active pharmaceutical ingredients, wherein the plurality of active pharmaceutical ingredients comprises an antacid, antidiarrheal, antiemetic, antiflatulent, stomach acidifier, or overindulgence reliever; and a plurality of botanical ingredients, wherein the plurality of botanical ingredients comprises cooked isomalt, elderberry tincture, honey, tartaric acid, marshmallow powder, lemon oil, Echinacea extract, tinofend stevia, and thyme oil, and wherein the plurality of active pharmaceutical ingredients and the plurality of botanical ingredients are present in a ratio by weight of about 1:5 to 1:11. Further provided herein are compositions wherein the plurality of active pharmaceutical ingredients and the plurality of botanical ingredients are present in a ratio by weight of about 1:7.5. Further provided herein are compositions wherein the plurality of active pharmaceutical ingredients and the plurality of botanical ingredients are present in a ratio by weight of 1:7.5. Further provided herein are methods for prevention, amelioration or treatment of a disease state associated with a digestive illness, comprising administering to a subject in need thereof a composition described. Further provided herein are methods further comprising administering an effective amount of the plurality of active pharmaceutical ingredients to prevent, ameliorate or treat a disease state associated with a digestive illness. Further provided herein are devices for digestive relief, comprising: a) a mixture for digestive relief comprising: i) a composition described; and ii) a solution in fluid communication with the plurality of active pharmaceutical ingredients; and b) a container enclosing the mixture. Further provided herein are devices for digestive relief, comprising: a) a mixture for digestive relief comprising: i) a composition described; and ii) a solution in fluid communication with the plurality of botanical ingredients; and b) a container enclosing the mixture.

BRIEF DESCRIPTION OF THE DRAWINGS

Present embodiments have other advantages and features which will be more readily apparent from the following detailed description and the appended claims, when taken in conjunction with the accompanying drawings, in which:

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

Throughout this disclosure, various embodiments can be presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 15%, 14%, 13%, 12%, 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Cough, Cold, Sore Throat and Allergy Relief

Figure 1:
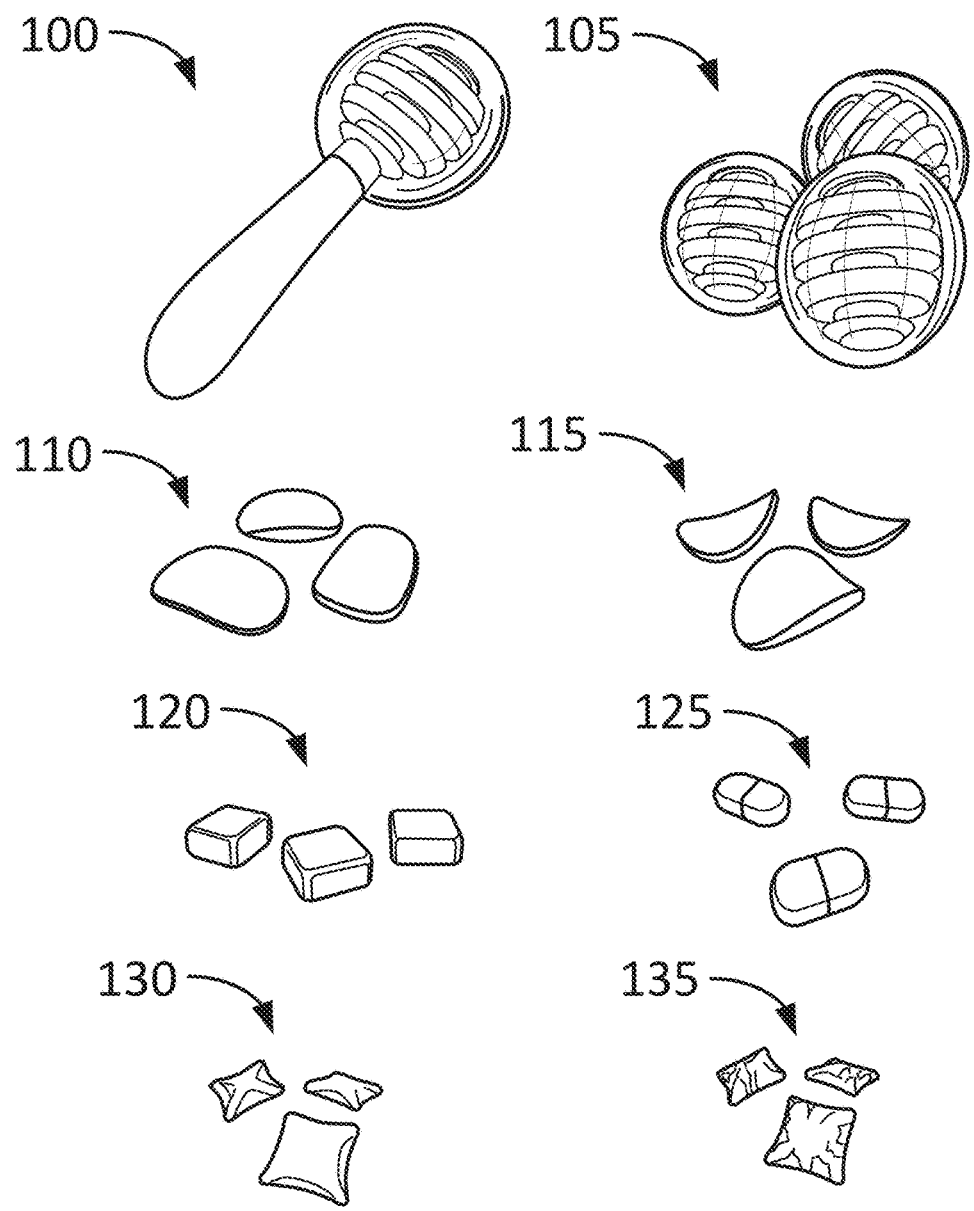
FIG. 1 illustrates an inner/outer ingredient arrangement, ergonomic, split dose, and liquid center configuration.
Figure 2:
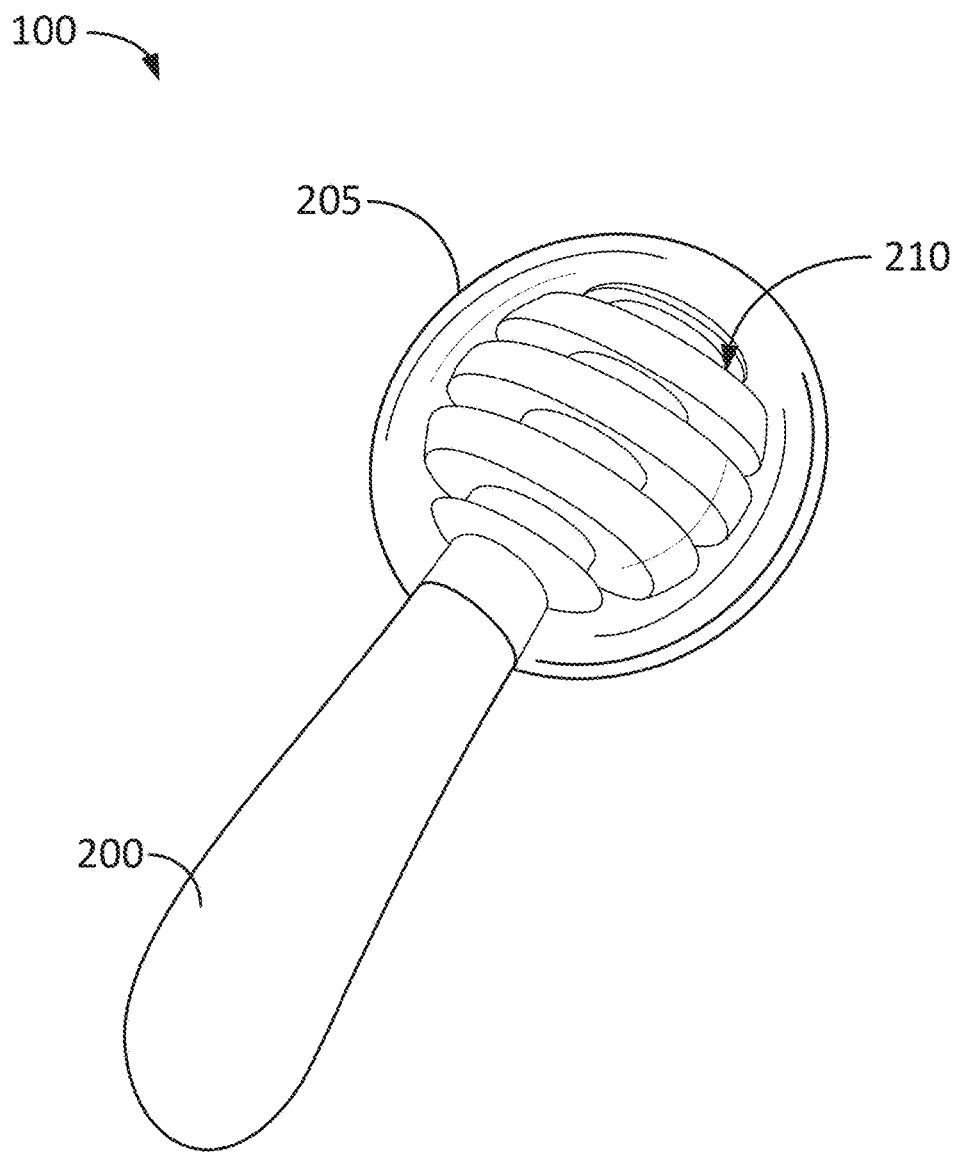
FIG. 2 illustrates a lollipop-like form.
Figure 3:
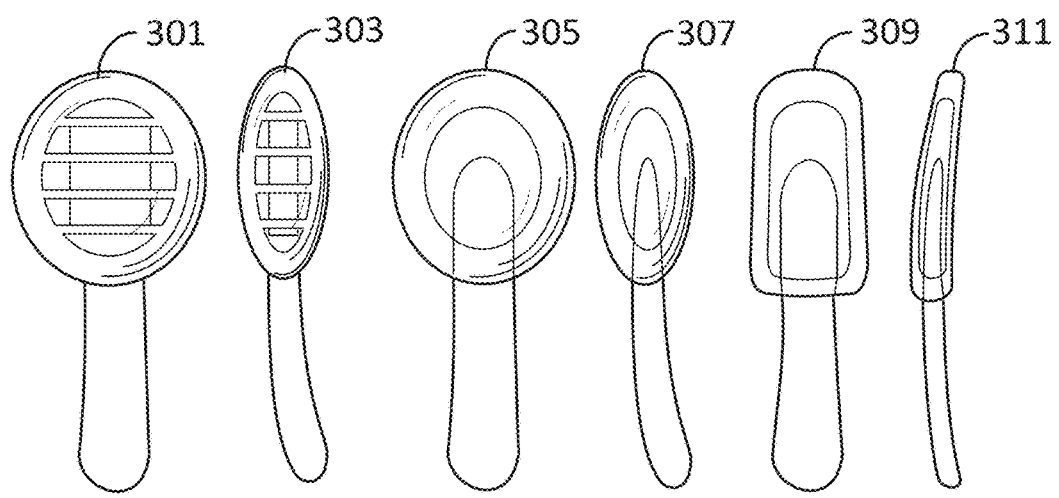
FIG. 3 illustrates variations in the head of the lollipop-like form.

Methods, compositions, devices and systems are described herein for the prevention, amelioration, and/or treatment of a cough, cold, sore throat, allergy or a related symptom. Described herein are combination products including a plurality of active pharmaceutical ingredients and a plurality of botanical ingredients. Exemplary dosage forms are illustrated in FIG. 1. The combination products may be in the form of a lollipop 100, lozenge 105, ergonomically shaped lozenge 110, 115, a split dose form of separate lozenges 120, a split does form where each lozenge comprises separate matrices 125 or pouch, a lozenge having a liquid center 130 or a pouch having a liquid center 135. A close up of an exemplary lollipop is illustrated in FIG. 2, which includes an ergonomic handle 200 and outer layer 205 and an inner layer 210. The lollipop head may also be ergonomically shaped for comfort. Exemplary ergonomically shaped head variations are illustrated in FIG. 3, which include a thin disc outer layer and an inner ridged core layer (front view 301 and side view 303); a thin disc outer layer and a solid inner core layer (front view 305 and side view 307); and an elongated curved outer layer and a smaller elongated and curved interior layer (front view 309 and side view 311).

Combination products described herein provide for improved, more palatable, and/or more soothing relief for a cough, cold, allergy, sore throat, allergy, or a related symptom, compared to a product including the one or more active pharmaceutical ingredients without the addition of a botanical ingredient or combination of botanical ingredients as described herein.

Dosage forms are provided herein wherein an active pharmaceutical ingredient described herein and a botanical ingredient described herein are in the same or different matrices. For example, in some cases, an outer layer comprises one or more botanical ingredients, and an inner layer comprising one or more active pharmaceutical ingredients. In some arrangements, a handle extending from the inner layer through the outer layer, wherein the outer layer surrounds the inner layer. In addition, devices are provided herein comprising a composition described herein. In some arrangements, both the inner layer and the outer layer comprise an active pharmaceutical ingredient and/or a botanical ingredient. Combination products provided herein may also provide multi-symptom relief to symptoms associated with cough, cold, sore throat, allergy or a related symptom of such illness.

Active Pharmaceutical Ingredients

The term "active pharmaceutical ingredient" (API) refers to a compound or pharmaceutically acceptable salt thereof, or a composition that prevents, treats, or ameliorates a cough, cold, sore throat or a related symptom. In addition, "active pharmaceutical ingredient" also refers to a compound which prevents or ameliorates symptoms associated with an allergy. Provided herein are devices and compositions for relief of a cough, cold, sore throat, or allergy, or a related symptom where at least one active pharmaceutical ingredient is included. In some cases, the amount of active pharmaceutical ingredient is an effective amount to prevent, treat, or ameliorate a cough, cold, sore throat or a related symptom. In some cases, the presence of a botanical ingredient in a device or composition comprising the active pharmaceutical ingredient provides for an enhanced effect compared to a device or composition comprising the active pharmaceutical ingredient without the botanical ingredient. Exemplary active pharmaceutical ingredient classes for relief of cough, cold, sore throat, or allergy, or a related symptom include analgesic, anesthetic, antihistamine, antitussive, expectorant, decongestant, or demulcent. Exemplary active pharmaceutical ingredients for relief of cough, cold, sore throat, or allergy, or a related symptom include, without limitation, acetaminophen, alcohol, allyl isothiocyanate, aminophylline, ammonium chloride, antimony potassium, aspirin, atropa, belladonna, atropine, sulfate, beachwood, creosote, belladonna alkaloids, benzoin preparations, benzonatate, bornyl acetate (topical), brompheniramine maleate, caffeine, camphor, caramiphen edisylate, carbetapentane citrate, cedar leaf oil (topical), cetirizine, chlophedianol hydrochloride, chloral hydrate, chloroform, chlorpheniramine maleate, cod liver oil, codeine, codeine phosphate, codeine sulfate, creosote, beechwood, datura stramonium, dexbromopheniramine maleate, dexchlorpheniramine maleate, dextromethorphan, dextromethorphan hydrobromide, diphenhydramine citrate, diphenhydramine hydrochloride, dimenhydrinate, doxylamine succinate, elm bark, ephedrine, ephedrine hydrochloride, ephedrine sulfate, epinephrine, epinephrine bitartrate, epinephrine hydrochloride, ethylmorphine hydrochloride, eucalyptol, eucalyptus oil, euphorbia pilulifera, fexofenadine, ginseng, guaifenesin, horehound, hydrocodone bitartrate, ibuprofen, iodides, ipecac, levmetamfetamine, loratadine, menthol, metaproterenol sulfate methapyrilene fumarate, methapyrilene hydrochloride, methoxyphenamine hydrochloride, mustard oil (alltlishthiocyanate), naphazoline hydrochloride, neproxen, niacinamide, noscapine, noscapine hydrochloride, oxymetazoline hydrochloride (aqueous), passion flower extract, peppermint oil, phenindamine tartrate, pheniramine maleate, phenobarbital, phenylephrine bitartrate (effervescent), phenylephrine hydrochloride, phenylpropanolamine bitartrate, phenylpropanolamine hydrochloride, phenyltoloxamine dihydrogen citrate, phenyltoloxamine hydrochloride, pine tar preparations, potassium bromide, potassium guaiacolsulfonate, propylhexedrine, pseudoephedrine hydrochloride, pseudoephedrine sulfate, pyrilamine maleate, racephedrine hydrochloride, salicylamide, scopolamine aminoxide hydrobromide, sodium bromide, sodium citrate, squill preparations, terpin hydrate preparations, thenyldiamine hydrochloride, theophylline, theophylline calcium salicylate, theophylline sodium glycinate, theophylline anhydrous, thiamine hydrochloride, thonzylamine hydrochloride, thymol, tolu preparations, triprolidine hydrochloride, turpentine oil, and xylometazoline hydrochloride (aqueous). In some instances, an active pharmaceutical agent provides a benefit including, without limitation, a pain relief, anti-inflammation, anti-microbial/anti-bacterial, soothing/lubrication, or immune-boosting property. Exemplary anti-inflammatory active pharmaceutical ingredients include, without limitation, ketoprofen, ibuprofen, naproxen sodium, and aspirin. Exemplary anesthetic active pharmaceutical ingredients include, without limitation, benzocaine, lidocaine, dyclonine, and hexylresorcinol. Exemplary counterirritant anesthetic active pharmaceutical ingredients include, without limitation, menthol and camphor. Exemplary demulcent active pharmaceutical ingredients include, without limitation, pectin, glycerin, and honey. In some instance, an exemplary antitussive active pharmaceutical ingredient is menthol. In some instances, a composition disclosed herein comprises at least three active pharmaceutical ingredients for cough, cold, allergy, or sore throat relief.

Devices and composition are provided herein for sore throat relief comprising one or more botanical ingredients and one or more of an analgesic, anesthetic, antihistamine, antitussive, expectorant, decongestant, or demulcent. In some instances, a composition is provided for sore throat relief which comprises one or more botanical ingredients and aspirin, menthol, and benzocaine. In some instances, a composition is provided for sore throat relief which comprises one or more botanical ingredients and acetaminophen, menthol, and benzocaine.

Botanical Ingredients

The term "botanical ingredient" as used herein refers to a botanical product, plant product, natural product, herbal product, algae or marine-derived plant products as well as any extract taken from such products which prevents, treats, or ameliorates a cough, cold, sore throat, or allergy, or a related symptom, or provides a soothing experience or improvement in taste. In addition, "botanical ingredient" also refers to a plant product, natural product, herbal product, algae or marine-derived plant product as well as any extract taken from such products which have an impact on a subject that prevents or ameliorates symptoms associated with an allergy. Provided herein are devices and compositions for a cough, cold, sore throat or allergy relief where at least one botanical ingredient is included. In some cases, the amount of a botanical ingredient is an amount effective to prevent, treat, or ameliorate a cough, cold, sore throat or a related symptom. In some cases, the presence of an active pharmaceutical ingredient in a device or composition comprising a botanical ingredient provides for an enhanced effect compared to a device or composition comprising the active pharmaceutical ingredient without the botanical ingredient. In some cases, the enhanced effect is synergistic. Botanical ingredient described herein may also have one or more characteristics as an excipient to improve taste, flavor, absorption, and/or provide a soothing sensation when included in a composition disclosed herein. Exemplary botanical ingredients included in a composition described herein for cough, cold, allergy, or sore throat relief include, without limitation, andrographis, astragalus, barberry, belladonna, chamomile, calendula, catnip glycerin, cayenne pepper, cinnamon powder, chamomile, turmeric, curcumin, drosera, Echinacea, elderberry, ginger goldenseal, ginger, glycerin, horehound, honey, isomalt (cooked), lavender, laurocerasus, lemon balm, lemon oil, licorice, marshmallow (powder), meadowsweet, oats, pectin, spilanthes, seaweed algae (red, brown, and green), sage, slippery elm, tartaric acid, thyme essential oil, tinofend, turmeric (Curcumin), mint, propolis, pelargonium sidoides, rumex crispus, Senega Officinalis, stevia, thyme oil, Verbascum Thapsus, and white willow bark.

Provided herein are devices and compositions including a botanical ingredient that provides pain relief, anti-inflammation relief, anti-microbial relief, anti-bacterial relief, a soothing/lubrication sensation, or an immune-boosting property. Table 1 provides an exemplary listing of botanical ingredients and relief characteristics.

TABLE 1

List botanical ingredients for sore throat

| Botanical ingredient | Relief characteristic |
| --- | --- |
| Andrographis | Preventing or treating colds |
| Barberry | Antimicrobial |
| Calendula | Immune-boosting; Promotes lymph circulation |
| Cayenne pepper | Analgesic |
| Chamomile | Calming effect |
| Echinacea | Immune-boosting |
| Elderberry | Antiviral |
| Goldenseal | Antimicrobial |
| Ginger | Anti-nausea; anti-microbial |
| Horehound | Astringent |
| Honey | Antimicrobial |
| Licorice | Demulcent |
| Marshmallow | Mucilaginous, soothing |
| Spilanthes | Numbing; Immune-boosting |
| Sage | Astringent |
| Slippery Elm | Mucilaginous, soothing |
| Thyme essential oil | Antimicrobial |
| Turmeric (Curcumin) | Anti-inflammatory |
| Propolis | Antimicrobial; Anti-inflammatory; Immune-boosting; Helps herbs stick to throat |
| Pelargonium sidoides | Anti-inflammatory |
| Maple leaf/branch | Immune-boosting |

Provided herein are compositions having an enhanced therapeutic effect in the prevention, treatment, or amelioration for a cough, cold, sore throat, or allergy, or a related symptom compared to administration of the active pharmaceutical ingredient without the botanical ingredient. In some instances, the presence of a botanical ingredient enables a lower dosage of active pharmaceutical ingredient administered than would be required for a similar therapeutic effect compared to administration of the active pharmaceutical ingredient without the botanical ingredient. In some instances, the combination of ingredients provides a synergistic effect such that a lesser amount of the active pharmaceutical ingredient is required for an improved result as compared to using the active pharmaceutical ingredient without the botanical ingredient. In some cases, the same amount of active pharmaceutical ingredient used with a botanical ingredient has a greater therapeutic effect on a subject as compared to using the active pharmaceutical ingredient without the botanical ingredient. It is understood that, depending on the desired properties, ingredients included can be altered in terms of which are included and in terms of amount included, e.g., to address a particular symptom, consider the prescription regimen of a subject, or in light of a subject's sensitivities to certain compounds (e.g., allergic reactions or metabolic regulation/processing). In some cases, the botanical ingredient uses a similar mechanism of action as the active pharmaceutical ingredient.

In some instances, the enhanced therapeutic effect is synergistic. In some instances, the synergistic ratio is about 1:0.1, 1:0.5, 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:150, 1:200, 1:300, 1:500, 1:1000 (by weight) or more. In some instances, the enhancement is 0.1 to 1 fold, 1 to 2 fold, 2 to 5 fold or more. In some cases, the combination of ingredients provides a synergistic effect such that a lesser amount of the active pharmaceutical ingredient is required for a similar result as compared to using the active pharmaceutical ingredient without the botanical ingredient.

In some cases, the presence of a botanical ingredient improves the bioavailability, increases the absorption, alters the metabolic processing, alters the rate of excretion or decreases toxicity of an active pharmaceutical ingredient disclosed herein. Reference herein made to "enhancement" in toxicity refers to a reduction in a toxic effect resulting from delivery of active pharmaceutical ingredient. In some cases, the presence of a botanical ingredient results in coating the stomach lining and thereby reduces the side effects of an active pharmaceutical ingredient disclosed herein. In some cases, the botanical ingredient uses a similar mechanism of action as the active pharmaceutical ingredient.

In some cases, the effect is on the bioavailability (the fraction ingested that is available for utilization in normal physiologic functions and for storage), bioconversion (the fraction ingested that is converted into an active form), bioefficacy (a measure of the biological efficacy of an active ingredient of drug; it is determined by the minimum dose required for maximum control of the disease), or the bioaccessibility (the fraction ingested that is released from food matrix and is available for intestinal absorption) of the active pharmaceutical ingredient. In some instances, the combination of a botanical ingredient and an active pharmaceutical ingredient has an enhancement effect on the bioavailability, bioconversion, bioefficacy, or bioaccessibility of the active pharmaceutical ingredient. In some instances, the enhancement is synergistic.

Dosage Amounts

In some instances, the amount of a botanical ingredient in a composition disclosed herein is within the range of 0.001-0.01, 0.01-0.1, 0, 1-1.0, 1.0-5.0, 5.0-10. 10-50, 50-100, 100-200, 200-500, 500-1,000, 1,000-2,000, or 2000-10,000 ug. In some instances, the amount of a botanical ingredient in a composition disclosed herein is at least about 1, 5, 10, 50, 100, 250, 500, 750, 1000, 2000, 3000, 4000, 5000, 6000, 8000, 10000, 15000, 20000 or more mg. In some instances, the total amount of botanical ingredients in a composition disclosed herein is at least about 1000, 5000, 7500, 10000, 12000, 12200, 12500, 12700, 13000, 15000, 20000, 21000, 22000 or more mg.

In some instances, the amount of an active pharmaceutical ingredient in a composition disclosed herein is within the range of 0.001-0.01, 0.01-0.1, 0, 1-1.0, 1.0-5.0, 5.0-10. 10-50, 50-100, 100-200, 200-500, 500-1,000, 1,000-2,000, or 2000-10,000 ug. In some instances, the amount of active pharmaceutical ingredient in a composition disclosed herein is at least about 1, 1.5, 2, 5, 10, 50, 100, 250, 325, 500, 750, 1000 or more mg. In some instances, the total amount of active pharmaceutical ingredient in a composition disclosed herein is at least about 50, 75, 85, 100, 15, 200, 300, 325, 500, 600, 675, 700, 800 or more mg.

In some instances, a composition disclosed herein comprises one or more active pharmaceutical ingredient and one or more botanical ingredient present in a total ratio by weight of about 1:20, 1:125, 1:30, 1:50, 1:100 or less. In some instances, a composition disclosed herein comprises one or more active pharmaceutical ingredient and one or more botanical ingredient present in a total ratio by weight of about 1:32 to 1:65. In some instances, a composition disclosed herein comprises one or more active pharmaceutical ingredients and one or more botanical ingredient present in a total ratio by weight of 1:64.

In some instances, a composition disclosed herein comprises a plurality of active pharmaceutical ingredients that are each an analgesic, antihistamine, antitussive, expectorant, nasal decongestant, or demulcent, wherein the plurality of active pharmaceutical ingredients is present in an amount of about 80 to 700 mg. In some cases, the composition further comprises a plurality of botanical ingredients, wherein the plurality of botanical ingredients is present in an amount of about 5000 to 22000 mg.

Provided herein is a composition for sore throat relief, comprising aspirin or acetaminophen present in an amount of about 200 to 800 or about 325 to 650 mg; menthol present in an amount of about 5 to 10 mg; benzocaine present in an amount about 2 to 15 mg; cooked isomalt present in an amount of about 18000 to 21000 mg; elderberry tincture present in an amount of about 1000 to 1200 mg; honey present in an amount of about 400 to 600 mg; tartaric acid present in an amount of about 30 to 60 mg; marshmallow powder present in an amount of about 30 to 60 mg; lemon oil present in an amount of about 10 to 30 mg; Echinacea extract present in an amount of about 8 to 16 mg; tinofend present in an amount of about 5 to 15 mg; Stevia (40%) present in an amount of about 5 to 15 mg; and thyme oil present in an amount of about 1 to 10 mg. Provided herein is a composition for sore throat relief, comprising aspirin or acetaminophen present in an amount of about 325 mg; menthol present in an amount of about 6 mg; benzocaine present in an amount about 5 mg; cooked isomalt present in an amount of about 19974 mg; elderberry tincture present in an amount of about 1100 mg; honey present in an amount of about 440 mg; tartaric acid present in an amount of about 55 mg; marshmallow powder present in an amount of about 40 mg; lemon oil present in an amount of about 20 mg; Echinacea extract present in an amount of about 12 mg; tinofend present in an amount of about 10 mg; Stevia (40%) present in an amount of about 9 mg; and thyme oil present in an amount of about 4 mg. In some cases, the composition is in the form of a lollipop.

Provided herein is a composition for sore throat relief, comprising aspirin or acetaminophen present in an amount of about 70 to 90 mg; menthol present in an amount of about 0.5 to 3 mg; benzocaine present in an amount about 0.5 to 3 mg; cooked isomalt present in an amount of about 4000 to 6000 mg; elderberry tincture present in an amount of about 200 to 400 mg; honey present in an amount of about 50 to 300 mg; tartaric acid present in an amount of about 5 to 20 mg; marshmallow powder present in an amount of about 5 to 20 mg; lemon oil present in an amount of about 1 to 10 mg; Echinacea extract present in an amount of about 1 to 10 mg; tinofend present in an amount of about 0.5 to 5 mg; Stevia (40%) present in an amount of about 0.5 to 5 mg; and thyme oil present in an amount of about 0.5 to 5 mg. Provided herein is a composition for sore throat relief, comprising aspirin or acetaminophen present in an amount of about 81.25 mg; menthol present in an amount of about 1.5 mg; benzocaine present in an amount about 1.25 mg; cooked isomalt present in an amount of about 4993.5 mg; elderberry tincture present in an amount of about 275 mg; honey present in an amount of about 110 mg; tartaric acid present in an amount of about 13.75 mg; marshmallow powder present in an amount of about 10 mg; lemon oil present in an amount of about 5 mg; Echinacea extract present in an amount of about 3 mg; tinofend present in an amount of about 2.5 mg; Stevia (40%) present in an amount of about 2.25 mg; and thyme oil present in an amount of about 1 mg. In some cases, the composition is in the form of a lozenge.

Dosage Forms

It will be appreciated that the ingredients disclosed herein be present in the same unit dosage form or as separate unit dosage forms. Compositions existing as separate unit dosage forms may be administered simultaneously or sequentially, depending on the desired application. Where a single unit dosage form includes one or more active pharmaceutical ingredients and one or more botanical ingredients, the ingredients may be in the same matrix or in different matrices. In some cases ingredients used for compositions disclosed herein are available for therapeutic intervention at different time points. In some cases ingredients disclosed herein are ingested sequentially.

In a first exemplary arrangement, a composition is provided which has an outer layer comprising a botanical ingredient layer and an inner layer comprising an active pharmaceutical ingredient layer. In further cases, the inner layer is encapsulated by the outer layer, e.g., 105. In some instances, a composition is provided which has a first layer comprising a botanical ingredient, a second layer comprising an active pharmaceutical ingredient. In some instances, the organization of the layers takes the form of a pattern. Exemplary patterns include, without limitation, a swirl, pinwheel, waves, stars, poke-a-dots, and stripes. In some instances, the layers are not organized in a structured pattern. In some instances, the layers are organized in a blended arrangement where microstructures exist within a larger layer. Exemplary microstructures include, without limitation, spherules, pellets, beads, crystals and vesicles. Alternatively, a botanical ingredient and an active pharmaceutical ingredient may exist in the same layer. In some instances, the inner layer has a shape that maximizes surface area between the two layers. For example, in FIG. 2, the inner layer 210 has a several ridged inlets. In some instances, the inner layer is in the form of a plurality of microstructures. Exemplary microstructures include, without limitation, bubbles, spheres, ovals, rectangles, squares, stars, stripes, and pinwheels.

Provided herein are dosage forms having components present in a liquid, gelatinous, semi-solid or solid state. Matrices provided herein may be in the same or different physical state. In some instances, an outer layer is solid, semi-solid, gelatinous or chewy. In some instances, an interior layer is liquid, solid, semi-solid, or gelatinous or chewy. In some cases, the overall form is that of a lollipop, lozenge, chewable tablet, frozen popsicle, dissolvable strip (e.g., by temperature and/or fluid contact), liquid filled hard candy, chewy ("gummy") form, hot or cold beverage. In some instances, an ingredient disclosed herein is in the form of a powder, pellet, bead, spherule, crystal, encapsulated in a carrier layer or dissolved in solution.

Provided herein are compositions having a matrix in a chilled or heated state. For example, a composition is provided which has an outer layer comprising a botanical ingredient, and an inner layer comprising an active pharmaceutical ingredient, and both layers are provided in a frozen form. In some instances, the composition is shelf stable and, once frozen (e.g., placed at a temperature at or below zero degrees Celsius), provides additional relief resulting from the cool temperature of the composition. Exemplary additional relief from cold temperature includes, without limitation, a numbing sensation, pain relief, and reduction in soft tissue swelling in the mouth.

In another example, a composition is provided which has an outer layer comprising a botanical ingredient, and an inner layer comprising an active pharmaceutical ingredient, and the active pharmaceutical ingredient is provided at warm or hot temperature, e.g., greater than 21 degrees Celsius. In some instances, the active pharmaceutical ingredient is shelf stable and, once warmed up (e.g., heated to a temperature at or above room temperature), provides an additional relief Exemplary additional relief from the warm temperature includes, without limitation, a soothing sensation and pain relief. In some instances, the composition comprises a handle which extends through the outer layer into the inner layer, and the handle has an opening for injection of the active pharmaceutical ingredient or botanical ingredient into the inner layer. In some cases, the injected ingredient is warmed prior to injection into the inner layer.

In another example, a device is provided which a matrix comprising one or more botanical ingredients and one or more active pharmaceutical ingredients, and a handle extending into the matrix. When stirred in a fluid, the matrix dissolves and releases the one or more botanical ingredients and one or more active pharmaceutical ingredients.

Dosage forms described herein may be delivered at various time intervals. For example, a dosage form described herein comprising a composition described herein may be administered 1, 2, 3, 4, 5, 6, 7, 8 or more times daily. In some instances, a dosage form described herein comprising a composition described herein may be administered every 30 minutes, hour, two hours, three hours, four hours, 6 hours, 8 hours, 12 hours or less frequently.

Applications

Provided herein are compositions to prevent, ameliorate, treat, or lesson a cold, cough, sore throat, a related illness, or allergy, or related symptoms thereof. Sources of the cold include, without limitation, viruses from the following: parainfluenza virus, rhinovirus, respiratory syncytial virus, enteroviruses, picornavirus, and coronavirus, metapneumovirus, and adenovirus. In some instances, the symptoms of the cold or a related illness include a sore throat, a cough, chest congestion, nasal congestion, a runny nose, muscle ache, fatigue, fever, loss of appetite, and headache. In some instances, the related illness is a microbial or bacterial infection (e.g., a streptococcal infection and acute bronchitis). A sore throat may be caused by or related to interaction with variety of sources, including, without limitation, viral sources (e.g., the common cold, laryngitis, mononucleosis, mumps, herpangina, and influenza), bacterial sources (e.g., strep throat, an inflammation or infection of the tonsils (tonsillitis) or the adenoids (adenoiditis), infection of the tissues around the tonsils (peritonsillar abscess), inflammation of the epiglottis (epiglottitis), inflammation of the uvula (uvulitis), irritation from low humidity, smoking, air pollution, yelling, or nasal drainage down the back of the throat (postnasal drip), allergies (e.g. from dust and pollen) or a stuffy nose, and chronic fatigue syndrome, a condition that causes extreme tiredness. In some instances, a composition described herein targets a portion of the body involved with a cold, cough, sore throat, or allergy, or a related condition. Exemplary sites for therapeutic targeting include, without limitation, the mouth, salivary glands, esophagus, sinuses, trachea, bronchial tubes, and structures inside the lungs.

In some instances, processes for manufacturing are provided which include combining one or more botanical ingredients described herein and one or more active pharmaceutical ingredients described. In some cases, kits are provided for cold, cough, sore throat and/or allergy relief include a composition described herein. In some cases, use of a combination of an active pharmaceutical ingredient and a botanical ingredient disclosed herein is for the preparation of a medicament for use in the prevention, treatment or amelioration of a cold, cough, sore throat, or allergy, or a related symptom.

Digestive Relief

Figure 4:
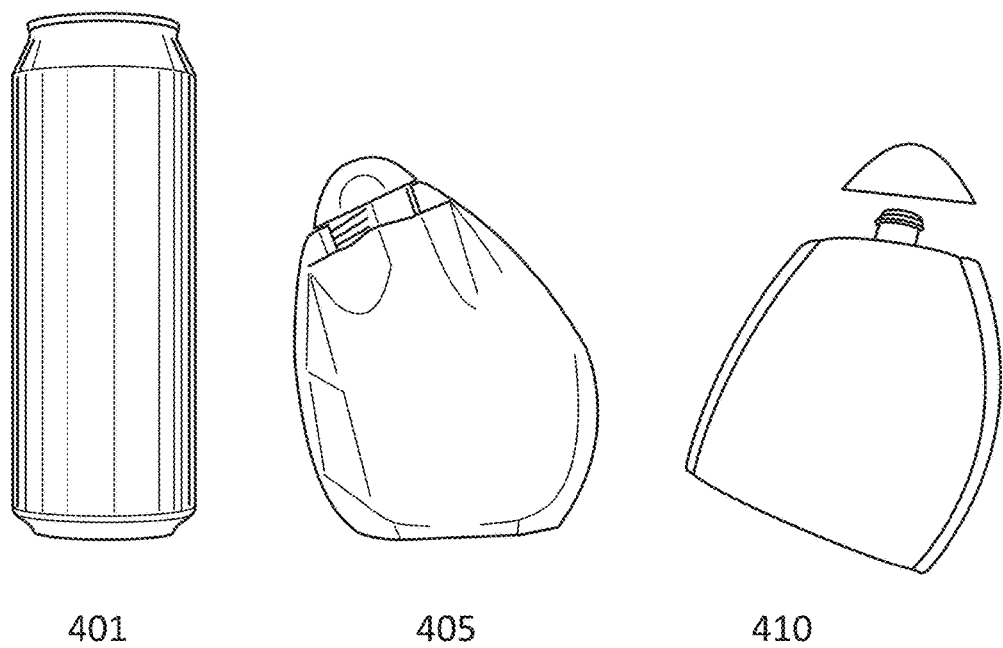
FIG. 4 illustrates a can, a soft pouch, and a hard pouch.

Methods, compositions, devices and systems are described herein for the prevention, amelioration, and/or treatment a digestive illness, digestive discomfort, or a related symptom. Described herein are combination products including one or more active pharmaceutical ingredients and one or more botanical ingredients. Exemplary containers for compositions described herein are illustrated in FIG. 4. Compositions may be provided a fluid or slurry form for delivery via a can 401, a high compressible pouch 405 (e.g., one that does not rebound to its original form after release of compression and optionally has a tear off lid), or hard pouch 410 (e.g., one that rebounds to its original form after release of compression).

Figure 5:
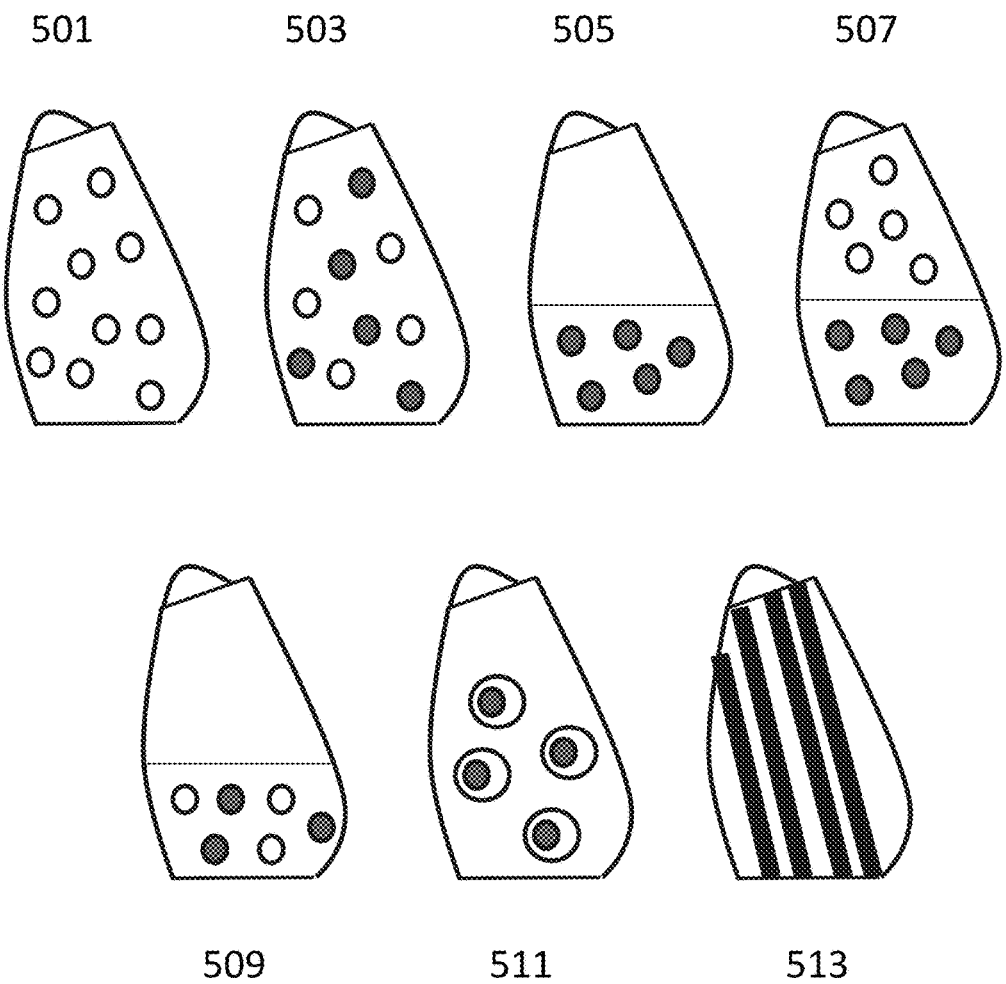
FIG. 5 illustrates arrangements for ingredients within a pouch container form.

Provided herein are compositions wherein the ingredients are present in different arrangements. Exemplary arrangements are illustrated in FIG. 5. In a first exemplary arrangement, ingredients are uniformly blended in a liquid, either as one type of particulate comprising both the active pharmaceutical ingredients and the botanical ingredients 501, or as separate population of particulates 503 for the active pharmaceutical ingredient and the botanical ingredient populations. In another exemplary arrangement, a barrier is included. In some instances, a liquid is present on either side of the barrier and microspheres containing an active pharmaceutical ingredient or a botanical ingredient are present on one side of the barrier, while the other side of the container lacks microspheres and contains an active pharmaceutical ingredient or a botanical ingredient 505. In some instances, a liquid is present on either side of the barrier and microspheres containing an active pharmaceutical ingredient are located on one side of the barrier and microspheres containing a botanical ingredient are located on the other side of the barrier 507. In some instances, microspheres containing an active pharmaceutical ingredient or a botanical ingredient are together uniformly distributed in a container on one side of a barrier 509. In some instances, vesicles containing an active pharmaceutical ingredient and a botanical ingredient are uniformly distributed in a container 511. In some instances, a gel includes two different matrices where one matrix includes an active pharmaceutical ingredient and another matrix includes a botanical ingredient 513.

Active Pharmaceutical Ingredients

The term "active pharmaceutical ingredient" (API) as used herein refers to a compound or pharmaceutically acceptable salt thereof, or a composition, that prevents, treats, or ameliorates a digestive illness or related symptom. Provided herein are devices and compositions for digestive relief where at least one active pharmaceutical ingredient is included. In some cases, the amount of active pharmaceutical ingredient is an effective amount to prevent, treat, or ameliorate a digestive illness or related symptom. In some cases, the presence of a botanical ingredient in a composition comprising the active pharmaceutical ingredient provides for an enhanced effect compared to a composition comprising the active pharmaceutical ingredient without the botanical ingredient. Exemplary antacid active pharmaceutical ingredients ingredients include, without limitation, aluminum carbonate gel (basic), aluminum hydroxide, aluminum hydroxide-hexitol, stabilized polymer, aluminum hydroxide-magnesium carbonate (co-dried gel), aluminum hydroxide-magnesium trisilicate (co-dried gel), aluminum hydroxide-sucrose powder hydrated, aluminum phosphate, aluminum phosphate gel, basic aluminum carbonate gel, bicarbonate, bismuth aluminate, bismuth carbonate, bismuth sodium tartrate, bismuth subcarbonate, bismuth subgallate, bismuth subnitrate, calcium carbonate, calcium phosphate, calcium polycarbophil, charcoal (activated), dihydroxyaluminum sodium carbonate, glycine (aminoacetic acid), hydrate magnesium aluminate activate sulfate, magaldrate, magnesium aluminosilicates, magnesium carbonate, magnesium glycinate, magnesium hydroxide, magnesium oxide, magnesium trisilicate, milk solids (dried), potassium carbonate, sodium bicarbonate, sodium carbonate, sodium potassium tartrate, tartrate (acid or salt), tricalcium phosphate and woodruff Exemplary active pharmaceutical ingredients for overindulgence in alcohol or food include, without limitation, acetaminophen, aluminum hydroxide, aluminum hydroxide gel, aspirin, bismuth subsalicylate, caffeine, fructose, magnesium carbonate, magnesium trisilicate, sodium citrate in solution and sodium acetylsalicylate (in solution). Exemplary digestive aid active pharmaceutical ingredients include, without limitation, alcohol, almadrate sulfate, aluminum hydroxide, amylase, anise seed, asafetida, *aspergillus oryza* enzymes, *bacillus acidophilus*, bean, belladonna alkaloids, belladonna leaves (powdered extract), betaine hydrochloride, bismuth subcarbonate, bismuth subnitrate, bismuth subgallate, blessed thistle (*Cnicus benedictus*), buckthorn, calcium carbonate, calcium gluconate, capsicum, capsicum (fluid extract of carbon), carbon, cascara sagrada extract, catechu (tinctures), catnip, cellulase, chamomile flowers, charcoal (wood/activated), chloroform, cimetidine, cinnamon oil, cinnamon tincture, citrus pectin, diastase malt, dihydroxyaluminum sodium carbonate, dog grass, duodenal substance, ether, esomeprazole, famotidine, fennel acid, galega, garlic, ginger, glycine, hectorite, homatropine methylbromide, huckleberry, horsetail, hydrastis canadensis (golden seal), hydrastis (fluid extract), hydrochloric acid, iodine, iron ox bile, johnswort, juniper tar, koalin (colloidal), knotgrass, lactic acid, lactose, lansoprazole, lysine hydrochloride, magnesium hydroxide, magnesium trisilicate, mannitol, mycozyme, myrrh (fluid extract), niacinamide, nitromersol, nux vomica extract, omeprazole, orthophosphoric acid, ox bile extract, pancreatin, pancrelipase, pectin, peppermint, peppermint oil, peppermint spirit, pepsin, phenacetin, potassium bicarbonate, potassium carbonate, prolase, protease, rhubarb fluid extract, senna, simethicone, sodium bicarbonate, sodium chloride, sodium citrate, sodium salicylate, sorbitol, stem bromelain strawberry, strychnine and tannic acid. Exemplary antidiarrheal active pharmaceutical ingredients include, without limitation, alumina powder (hydrated), bismuth subsalicylate, calcium gluconate, calcium polycarbophil, carboxymethylcellulose sodium, charcoal (activated), glycine, homatropine methylbromide, hyocyamine sulfate, kaolin, *lactobacillus acidophilis*, *lactobacillus bulgaricus*, loperamine HCl, opium powder, opium tincture, paregoric, pectin, phenyl salicylate (salo), psyllium husk, polycarbophil, potassium carbonate, scopolamine hydrobromide, sodium carboxymethylcellulose, and zinc phenolsulfonate. Exemplary active pharmaceutical ingredients for nausea include, without limitation, bismuth subsalicylate, phosphorylated sugars, doxylamin succinate, diphenhydramine, meclizine, odium citrate dehydrate, calcium carbonate, dextrose, levulose, meclizine hydrochloride, and phosphoric acid. In some instances, a composition disclosed herein comprises at least two active pharmaceutical ingredients for digestive relief.

In some instances, an active pharmaceutical ingredient provides a medical effect including, without limitation, a pain relief, anti-inflammation, anti-parasitic, anti-bacterial, anti-fungal, or immune-boosting property. In some instances, an active pharmaceutical ingredient lessens the impact of symptoms such as abdominal pain, acid reflux, belching, nausea, vomiting, migraine, loss of appetite, fever, fatigue, abdominal bloating, early satiety, and abdominal distention, chest pain, diarrhea or flatulence. Exemplary anti-inflammatory active pharmaceutical ingredients include, without limitation, ketoprofen, ibuprofen, naproxen sodium, and aspirin. Exemplary anesthetic active pharmaceutical ingredients include, without limitation, benzocaine, lidocaine, dyclonine, and hexylresorcinol.

Botanical Ingredients

The term "herbal active ingredient" as used herein refers to a botanical product, natural product, herbal product, botanical, bacterial, algal or marine-derived plant product as well as an extract taken from such products which prevents, treats, or ameliorates a disease state associated with a digestive illness or related condition. Exemplary antacid botanical ingredients include, without limitation, black pepper, chicory root tea, cinnamon, ginger root, grapefruit skin extract, herbal tea, Indian gooseberry, lavender, licorice, orange peel, orange peel extract, marshmallow, mallow, pineapple, gamma oryzanol, clubmoss, celandine, Chilean sassafras, Pau d'Arco bark, natrum muriaticum, sepia and slippery elm. Exemplary botanical ingredients for overindulgence in alcohol or food include, without limitation, artichoke extract, kudzu root, prickly pear cactus extract. Exemplary digestive aid botanical ingredients include, without limitation, aloe vera, anise, bryonia, carbo vegetabilis, calamus, cardamom, cayenne, chamomile, dandelion, mint, metha, spearmint, fennel, garlic, gentian root, ginger, hops, horsetail, larch arabinogalactan, marshmallow plant, licorice, nux vomica, papaya, peppermint, pulsatilla, rosemary, thyme, tormentil, valerian plant and wormwood herb. Exemplary antidiarrheal herbal active ingredients include, without limitation, agave, agrimony, allspice, amur cork tree, andrographis, astragalus, barberry, bayberry, bilberry, bistort, black walnut, blackberry, blessed thistle, blueberry, boswellia serrata, bumet saxifrage, carob, coriander, cranesbill, dill, dwarf milkwort, Echinacea, European ash, fennel, fenugreek, fig, flaxseed, ginger, goldenseal, great bumet, heather, Iceland moss, *lactobacillus acidophilis*, lady's mantle, lavender, lemon grass, marshmallow root, meadowsweet, oregano, Oregon grape, picrorhiza kurroa, pleurisy root, pomegranate, psyllium, raspberry, *saccharomyces boulardii*, self heal, silverweed, slippery elm, vervain, yarrow and yellow dock. Exemplary botanical ingredients for nausea include, without limitation, activated charcoal, barley, bran, catnip, chamomile essential oil, chamomile, cinnamon, cloves, cucumber, dandelion, fennel tea, ginger, goldenseal, honey, horehound, lavender, essential oil, lemon juice, maple syrup, milk thistle seed, nutmeg, peppermint, peppermint essential oil, rosehips, spearmint, sweet basil, turmeric, yellow dock tea and yellow root.

Botanical ingredients for use in compositions for digestive relief may provide a benefit including, without limitation, a pain relief, anti-inflammation, anti-parasitic, anti-bacterial, anti-fungal, or immune-boosting property (e.g., maple leaf/branch). In some instances, a botanical ingredient lessens the impact of symptoms such as abdominal pain, acid reflux, belching, nausea, vomiting, migraine, loss of appetite, fever, fatigue, abdominal bloating, early satiety, and abdominal distention, chest pain, diarrhea or flatulence. For example, a compositions comprising the combination of Chamomile flower, peppermint, bitter candy tuft, licorice, caraway fruit, and lemon balm provides beneficial effects against irritable bowel syndrome (IBS).

In some instances, at least one botanical ingredient is included in a composition described herein. In some instances, the botanical ingredient is located in a discrete layer in a consumable beverage. In some instances, the botanical ingredient is located in the same layer as an active pharmaceutical ingredient. In some instances, the botanical ingredient is located in a distinct layer from a layer having an active pharmaceutical ingredient. In some instances, the botanical ingredient and the active pharmaceutical ingredient are in fluid communication.

Provided herein are compositions having an enhanced therapeutic effect in the prevention, treatment, or amelioration a digestive illness or a related symptom compared to administration of the active pharmaceutical ingredient without the botanical ingredient. In some cases, the presence of a botanical ingredient in a composition described herein enables a lower dose of an active pharmaceutical active ingredient to achieve a similar outcome compared to administration of the active pharmaceutical ingredient without the botanical ingredient. In some cases, the presence of a botanical ingredient improves the bioavailability, increases the absorption, alters the metabolic processing, or decreases toxicity of an active pharmaceutical ingredient disclosed herein. In some cases, the presence of a botanical ingredient results in coating the stomach lining and thereby reduces the side effects of an active pharmaceutical ingredient disclosed herein. In some cases, the botanical ingredient uses a similar mechanism of action as the active pharmaceutical ingredient.

In some instances, the enhanced therapeutic effect is synergistic. In some instances, the synergistic ratio is about 1:0.1, 1:0.5, 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:150, 1:200, 1:300, 1:500, 1:1000 (by weight) or more. In some instances, the enhancement is 0.1 to 1 fold, 1 to 2 fold, 2 to 5 fold or more. In some cases, the addition of a botanical ingredient with an active pharmaceutical ingredient provides for synergistic effect such that a lesser amount of the active pharmaceutical ingredient is required for a beneficial result as compared to using the active pharmaceutical ingredient without the botanical ingredient.

In some cases, the presence of a botanical ingredient improves the bioavailability, increases the absorption, alters the metabolic processing, alters the rate of excretion or decreases toxicity of an active pharmaceutical ingredient disclosed herein. In some cases, the effect is on the bioavailability (the fraction ingested that is available for utilization in normal physiologic functions and for storage), bioconversion (the fraction ingested that is converted into an active form), bioefficacy (a measure of the biological efficacy of an active ingredient of drug; it is determined by the minimum dose required for maximum control of the disease), or the bioaccessibility (the fraction ingested that is released from food matrix and is available for intestinal absorption) of the active pharmaceutical ingredient. In some instances, the combination of a botanical ingredient and an active pharmaceutical ingredient has a synergistic effect on the bioavailability, bioconversion, bioefficacy, or bioaccessibility of the active pharmaceutical ingredient.

In some cases, the presence of an herbal active ingredient increases the absorption of an active pharmaceutical ingredient such that a lesser amount of the active pharmaceutical ingredient is required for a similar therapeutic effect as compared to using the active pharmaceutical ingredient without the botanical ingredient. In some cases, the combination of ingredients increases the absorption of an active pharmaceutical ingredient such that a lesser amount of the active pharmaceutical ingredient is required for a greater therapeutic effect as compared to using the active pharmaceutical ingredient without the botanical ingredient. In some cases, the combination of ingredients increases the absorption of an active pharmaceutical ingredient such that the same amount of the active pharmaceutical ingredient, as compared to using the active pharmaceutical ingredient without the herbal active ingredient, results in greater therapeutic effect.

Dosage Amounts

In some instances, the amount of a botanical ingredient in a composition disclosed herein is within the range of 0.001-0.01, 0.01-0.1, 0, 1-1.0, 1.0-5.0, 5.0-10. 10-50, 50-100, 100-200, 200-500, 500-1,000, 1,000-2,000, or 2000-10,000 ug. In some instances, the amount of a botanical ingredient in a composition disclosed herein is at least about 1, 5, 10, 50, 75, 100, 250, 400, 500, 750, 1000, 2000, 3000, 4000, 4500, 5000, 5500, 6000, 8000, 10000, 15000, 20000 or more mg. In some instances, the total amount of botanical ingredients in a composition disclosed herein is at least about 1000, 5000, 7500, 10000, 12000, 12200, 12500, 12700, 13000, 15000, 20000, 21000, 22000 or more mg.

In some instances, the amount of an active pharmaceutical ingredient in a composition disclosed herein is within the range of 0.001-0.01, 0.01-0.1, 0, 1-1.0, 1.0-5.0, 5.0-10. 10-50, 50-100, 100-200, 200-500, 500-1,000, 1,000-2,000, or 2000-10,000 ug. In some instances, the amount of active pharmaceutical ingredient in a composition disclosed herein is at least about 1, 1.5, 2, 5, 10, 50, 100, 250, 325, 500, 750, 1000, 1500, 2000 or more mg. In some instances, the total amount of active pharmaceutical ingredient in a composition disclosed herein is at least about 500, 600, 675, 700, 800, 900, 1000, 1500, 1750, 2000, 2500, 3000 or more mg.

In some instances, a composition disclosed herein comprises one or more active pharmaceutical ingredient and one or more botanical ingredient present in a total ratio by weight of about 1:5, 1:7.5, 1:10, 1:11, 1:15, 1:20, 1:30, 1:50, 1:100 or less. In some instances, a composition disclosed herein comprises one or more active pharmaceutical ingredient and one or more botanical ingredient present in a total ratio by weight of about 1:5 to 1:1. In some instances, a composition disclosed herein comprises one or more active pharmaceutical ingredients and one or more botanical ingredient present in a total ratio by weight of 1:7.5.

In some instances, a composition disclosed herein comprises a plurality of active pharmaceutical ingredients that are each an comprises an antacid, antidiarrheal, antiemetic, antiflatulent, stomach acidifier, or overindulgence reliever, wherein the plurality of active pharmaceutical ingredients is present in an amount of about 1100 to 2500 mg, about 1100 to 2200 mg, or about 1600 to 2200 mg. In some cases, the composition further comprises a plurality of botanical ingredients, wherein the plurality of botanical ingredients is present in an amount of about 12000 to 13000 mg, or about 10000 to 15000 mg.

Provided herein is a composition for upset stomach relief, comprising: calcium carbonate or bismuth subsalicylate present in an amount of about 1000 to 2000 mg; simethicone present in an amount of about 50 to 200 mg; honey present in an amount about 5000 to 6000 mg; oats present in an amount of about 4000 to 5000 mg; catnip glycerine present in an amount of about 500 to 1000 mg; chamomile flower present in an amount of about 300 to 600 mg; marshmallow powder present in an amount of about 200 to 500 mg; meadowsweet present in an amount of about 200 to 500 mg; ginger present in an amount of about 100 to 300 mg; and turmeric present in an amount of about 50 to 150 mg. Provided herein is a composition for upset stomach relief, comprising: calcium carbonate or bismuth subsalicylate present in an amount of about 1500 mg; simethicone present in an amount of about 125 mg; honey present in an amount about 5400 mg; oats present in an amount of about 4500 mg; catnip glycerine present in an amount of about 747 mg;

chamomile flower present in an amount of about 590 mg; marshmallow powder present in an amount of about 393 mg; meadowsweet present in an amount of about 393 mg; ginger present in an amount of about 155 mg; and turmeric present in an amount of about 77 mg. In some cases, the composition is in the form of a cream or slurry.

Provided herein is a composition for upset stomach relief, comprising: calcium carbonate or bismuth subsalicylate present in an amount of about 1000 to 2000 mg; simethicone present in an amount of about 50 to 200 mg; honey present in an amount about 4000 to 5000 mg; meadowsweet present in an amount of about 2500 to 3500 mg; chamomile present in an amount of about 1500 to 2000 mg; lemon balm present in an amount of about 2000 to 3500 mg; and turmeric present in an amount of about 400 to 600 mg. In some cases, the composition is in the form of a tonic. Provided herein is a composition for upset stomach relief, comprising: calcium carbonate or bismuth subsalicylate present in an amount of about 1500 mg; simethicone present in an amount of about 125 mg; honey present in an amount about 4500 mg; meadowsweet present in an amount of about 3093 mg; chamomile present in an amount of about 1708 mg; lemon balm present in an amount of about 2814 mg; and turmeric present in an amount of about 585 mg. In some cases, the composition is in the form of a tonic.

Dosage Forms

In some cases, the arrangement of ingredients in a composition or device is part of an overall scheme to provide optimal delivery of a mixture of ingredients. In some cases, at least one ingredient is located within a liquid, slurry, gelatinous, semi-solid, or solid medium. In some cases, the medium is a solution. In some instances, the solution is clear or cloudy. In some instances, the solution is a cream-based medium. In some cases, the medium is carbonated, e.g., a tonic. In some instances, an ingredient disclosed herein is in the form of a powder, pellet, bead, spherule, crystal, encapsulated in a carrier layer or dissolved in solution.

In some cases, an active pharmaceutical ingredient and a botanical ingredient are in the same medium. In some cases, an active pharmaceutical ingredient and a botanical ingredient are in a separate media. In some cases, a removable barrier separates one media from another. Exemplary ways to remove the barrier include, without limitation, application of pressure, temperature, or enzymatic reaction. Example barriers include, without limitation, films, small capsules, vesicles or crystals. In some cases, the barrier isolates or separates a region from a medium. In some cases, the isolated region contains an active pharmaceutical ingredient or an herbal active ingredient. In some cases, the isolated region contains an active pharmaceutical ingredient and an herbal active ingredient. In some cases, the composition includes layers of material in a gelatinous state in which each layer has a different set of ingredients. In some cases the organization of the layers takes the form of a pattern. Exemplary patterns include, without limitation, a swirl, pinwheel, waves, lines, poke-a-dots, and stripes. In some cases, the layers are not organized in a structured pattern. In some cases, the layers are organized in a blended uniform arrangement.

In some instances, the arrangement of a solution or matrix holding ingredients disclosed herein contributes towards the beneficial effect on a subject derived from the combination of ingredients. In some instances, an ingredient disclosed herein is organized in a uniform arrangement within a liquid, slurry, gelatinous, semi-solid or solid matrix. In some instances, a botanical ingredient and an active pharmaceutical ingredient are uniformly blended in the liquid, slurry or gelatinous. In some instances, ingredients disclosed herein are located in discrete sections. In some cases, microstructures having an ingredient disclosed herein are organized within a liquid, slurry or gelatinous matrix. Exemplary microstructures include, without limitation, spherules, pellets, beads, crystals and vesicles.

In some cases, a composition disclosed herein is shelf stable and, once frozen (e.g., cooled to a temperature at or below zero degrees Celsius), provides an additional digestive relief. In some cases, a composition disclosed herein is shelf stable and, once heated (e.g., warmed to a temperature at or above 25 degrees Celsius), provides an additional relief. In some cases, a change in temperature results in the breakdown of a barrier or microstructure separating one ingredient from another.

In some cases, compositions or devices provided herein include a solid surrounding structure which provides a functional benefit for delivery of an active pharmaceutical ingredient and a botanical ingredient. Exemplary structures include, without limitation, a common drinking can, a pouch, a common yogurt container with a lid that can be unpeeled. The container optionally has an interior barrier which is removable. Exemplary applications to remove the barrier include, without limitation, stirring, heating, freezing, shaking, squeezing or puncturing at least of portion of the barrier.

In some cases, a barrier encapsulates an ingredient and the barrier is removed by enzymatic reaction. In some cases, an enzyme is capable of breaking down a microstructure, separating one ingredient from another. For example, a microstructure which is a chemical coating degraded in the presence of a digestive enzyme will, when ingested, release an ingredient encapsulated the microstructure. Similarly, in some cases, a microstructure which is a vesicle also degrades once in contact with a digestive enzyme.

In some cases, a container encapsulating ingredients described herein is ergonomically shaped such that it is comfortably hand-held. In some cases, the ergonomically-shaped container is easily compressible upon application of pressure. In some cases, the application of compression forces contents out of the container. In some cases, the container is designed such that it rebounds to its original shape after the release of application of compression.

Applications

Provided herein are compositions to prevent, ameliorate, or treat a digestive illness or a related symptom. Exemplary digestive illnesses include, without limitation, food allergies, food sensitivities, celiac disease, irritable bowel syndrome (IBS), overindulgence in food or alcohol, gastroesophageal reflux disease (GERD), ulcerative colitis, Crohn's disease, bacterial infection, parasitic infection and viral infection (e.g., gastroenteritis). Exemplary types of bacteria causing digestive disorders include, without limitation *Campylobacter jejuni, Escherichia coli, Salmonella, Shigella, Vibrio cholerae, Clostridium difficile,* and *Staphylococcus aureus*. Exemplary types of parasites causing digestive disorders include, without limitation, *Giardia lamblia, Entamoeba histolytica*, and certain species of *Cryptosporidium*. Exemplary types of viruses causing digestive disorders include, without limitation, norovirus, rotavirus, adenovirus, parvovirus and astrovirus. In some instances, compositions disclosed herein are used as part of a plan to prevent, treat or ameliorate a disease state or symptoms associated with digest illness. Exemplary symptoms associated with digestive illness or related condition include, without limitation, abdominal pain, acid reflux, belching, nausea, vomiting, migraine, loss of appetite, fever, fatigue, abdominal bloating, early satiety, and abdominal distention, chest pain, diarrhea or flatulence.

In some instances, a composition described herein targets a portion of the body involved with a digestive illness or related condition. Exemplary sites for therapeutic targeting include, without limitation, the mouth, salivary glands, esophagus, stomach, small intestine, large intestine, colon, rectum, liver, pancreas, and gallbladder.

In some instances, processes for manufacturing are provided which include combining one or more botanical ingredients described herein and one or more active pharmaceutical ingredients described. In some cases, kits are provided for digestive relief including a composition described herein. In some cases, use of a combination of an active pharmaceutical ingredient and a botanical ingredient disclosed herein is for the preparation of a medicament for use in the prevention, treatment or amelioration of a digestive illness or a related symptom.

Dosage forms described herein may be delivered at various time intervals. For example, a dosage form described herein comprising a composition described herein may be administered 1, 2, 3, 4, 5, 6, 7, 8 or more times daily. In some instances, a dosage form described herein comprising a composition described herein may be administered every 30 minutes, hour, two hours, three hours, four hours, 6 hours, 8 hours, 12 hours or less frequently.

Additives

Composition described herein may comprise a nutritional supplement, for example, a vitamin or mineral. In some instances, the nutritional supplement is located in the outer layer or inner layer of a lollipop or lozenge. In some instances, the nutritional supplement is located in solution of a fluid layer of a beverage. Exemplary nutritional supplements include, without limitation, vitamin $B_1$, vitamin $B_2$, vitamin $B_6$, vitamin $B_{12}$, folic acid, $D_3$, vitamin C, vitamin E, copper, zinc, iron, omega-3 fatty acids.

Provided herein are compositions including a botanical ingredient to enhance taste or mouth-feel of a composition described herein comprising an active pharmaceutical ingredient. Flavors may be used to mask unpleasant tasting ingredients. In some cases, a range of flavoring includes, without limitation, herbal/natural, medicinal/mentholated, and candy/confectionary/sweet. In preparing flavor profiles, techniques drawn from commercial food science are deployed to mask flavors and improve the tasting experience, for example by covering over the bitter or acrid taste of certain active pharmaceutical ingredients. Exemplary flavorings to improve a bitter API include, without limitation, mint, cherry and anise. Exemplary flavorings to improve a salty API include, without limitation, peach, apricot or licorice. Exemplary flavorings to improve a sour API include, without limitation, raspberry and licorice. In the case of an excessively sweet API, countering flavors include vanilla.

Provided herein are compositions which facilitate restoring a digestive tract from dysbiosis. In some instances, an ingredient included in a composition disclosed herein is a probiotic bacterium. Exemplary probiotic bacteria include, without limitation, *Lactobacillus acidophilus, Lactobacillus casei, Lactobacillus fermentum, Lactobacillus rhamnosu, Bifidobacteria bifidum, Bifidobacterium infantis*, and *Bifidobacteria longum*. In some instances, the combination of an active pharmaceutical ingredient and a botanical ingredient results in restoring a heathy (or non-pathogenic) balance of flora in the gut, also referred to as the microbiome. In some instances, the botanical ingredient includes prebiotics to selectively stimulate the growth and activity of intestinal bacteria associated with health and wellbeing. Exemplary prebiotic ingredient sources include, without limitation, chicory root, artichokes, dandelion greens, garlic, leeks, onions, asparagus, wheat bran, bananas, blueberries, raspberries, blackberries, strawberries, almonds, walnuts, cashews, pumpkin, sesame, and sunflower. In some instances, the combination of a botanical ingredient with an active pharmaceutical ingredient reduces the impact of the active pharmaceutical ingredient in creating bacterial disequilibrium in the gut, as compared to deliver of the active pharmaceutical ingredient without the botanical ingredient.

Excipients

Compounds disclosed herein may include at least one pharmaceutically acceptable excipient. Exemplary classes of excipients include, without limitation, antiadherents, binders, coatings, disintegrants, flavors, colors, lubricants, glidants, sorbents, preservatives, and sweeteners. Exemplary antiadherents include, without limitation, magnesium stearate, talc, cornstarch, colloidal silica, DL-leucine, sodium lauryl sulfate and stearates. Exemplary binders include, without limitation, saccharides and their derivatives: disaccharides (sucrose, lactose); polysaccharides and their derivatives (starches, cellulose or modified cellulose such as microcrystalline cellulose and cellulose ethers such as hydroxypropyl cellulose (HPC)); sugar alcohols such as xylitol, sorbitol or maltitol; protein: gelatin; synthetic polymers: polyvinylpyrrolidone (PVP), and polyethylene glycol (PEG). Exemplary coatings include, without limitation, cellulose ether hydroxypropyl methylcellulose (HPMC) film, shellac, corn protein zein and gelatin. Enterics control the rate of drug release and determine where the drug will be released in the digestive tract. Materials used for enteric coatings include fatty acids, waxes, shellac, plastics, and plant fibers. Exemplary disintegrants include, without limitation, crosslinked polymers: crosslinked polyvinylpyrrolidone (crospovidone), crosslinked sodium carboxymethyl cellulose (croscarmellose sodium); glycolate. Exemplary lubricants include talc, silica, and fats—e.g., vegetable stearin, magnesium stearate or stearic acid. Exemplary glidants include, without limitation, fumed silica, talc, and magnesium carbonate. Exemplary preservatives include, without limitation, antioxidants (e.g., vitamin A, vitamin E, vitamin C, retinyl palmitate, and selenium), amino acids (e.g., cysteine and methionine), citric acid and sodium citrate. Exemplary synthetic preservatives include, without limitation, methyl paraben and propyl paraben. In some instances, a botanical ingredient disclosed herein is an excipient.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1: Lollipop for Sore Throat Relief

A lollipop dosage form was manufactured and included a handle inserting into a head region. The head region included an outer region and an inner region. The handle has a curved ergonomic shape designed for easy holding. The head contained ingredients as listed in Table 2. The lollipop had a 22 g serving size and was measured to be 44 calories.

TABLE 2

| Ingredient | Amount per dose |
|---|---|
| Inner Region | |
| Aspirin | 325 mg |
| Menthol | 6 mg |
| Benzocaine | 5 mg |
| Layer Total: | 336 mg |
| Outer Region | |
| Cooked isomalt | 19974 mg |
| Elderberry tincture | 1100 mg |
| Honey | 440 mg |
| Tartaric acid | 55 mg |
| Marshmallow powder | 40 mg |
| Lemon oil | 20 mg |
| Echinacea extract | 12 mg |
| Tinofend | 10 mg |
| Stevia, 40% | 9 mg |
| Thyme oil | 4 mg |
| Layer Total: | 21664 mg |
| Weight of both layers: | 22000 mg |

In an alternative example, the aspirin is replaced with acetaminophen.

Example 2: Lozenge for Sore Throat Relief

A lozenge dosage form 115 was manufactured and contained a mixture of ingredients as listed in Table 3. The lozenge had a 5.5 g serving size and was measured to be 11 calories.

TABLE 3

| Ingredient | Amount per dose |
|---|---|
| Active Pharmaceutical Ingredients | |
| Aspirin | 81.25 mg |
| Menthol | 1.5 mg |
| Benzocaine | 1.25 mg |
| API Total: | 84 mg |
| Botanical Ingredients | |
| Cooked isomalt | 4993.5 mg |
| Elderberry tincture | 275 mg |
| Honey | 110 mg |
| Tartaric acid | 13.75 mg |
| Marshmallow powder | 10 mg |
| Lemon oil | 5 mg |
| Echinacea extract | 3 mg |
| Tinofend | 2.5 mg |
| Stevia, 40% | 2.25 mg |
| Thyme oil | 1 mg |
| Botanical Ingredient Total: | 5416 mg |
| Weight of both layers: | 5500 mg |

In an alternative example, the aspirin is replaced with acetaminophen.

Example 3: Beverage for Upset Stomach Relief

A beverage was manufactured having ingredients as listed in Table 4. The beverage had a 3 fluid ounce serving size and was measured to be 40 calories.

TABLE 4

| Ingredient | Amount per dose |
|---|---|
| Active Pharmaceutical Ingredients | |
| Calcium Carbonate | 1500 mg |
| Simethicone | 125 mg |
| API Total: | 1625 mg |
| Botanical Ingredients | |
| Honey | 5400 mg |
| Oats | 4500 mg |
| Catnip glycerin | 747 mg |
| Chamomile flowers | 590 mg |
| Marshmallow powder | 393 mg |
| Meadowsweet powder | 393 mg |
| Ginger powder | 155 mg |
| Turmeric | 77 mg |
| Botanical Ingredient Total: | 12255 mg |
| API + BI Total: | 13880 mg |

In an alternative example, the calcium carbonate is replaced with bismuth subsalicylate.

Example 4: Tonic Beverage for Upset Stomach Relief

A beverage was manufactured having ingredients as listed in Table 5. The beverage was carbonated. The beverage had a 3 fluid ounce serving size and was measured to be 20 calories.

TABLE 5

| Ingredient | Amount per dose |
|---|---|
| Active Pharmaceutical Ingredients | |
| Calcium Carbonate | 1500 mg |
| Simethicone | 25 mg |
| API Total: | 1625 mg |
| Botanical Ingredients | |
| Honey | 4500 mg |
| Meadowsweet | 3093 mg |
| Chamomile | 1708 mg |
| Lemon balm | 2814 mg |
| Turmeric | 585 mg |
| Botanical Ingredient Total: | 12700 mg |
| API + BI Total: | 14325 mg |

In an alternative example, the calcium carbonate is replaced with bismuth subsalicylate.

Example 5: Lollipop for Sore Throat Relief

A lollipop dosage form has an outer layer and an inner layer at the head of the pop. The outer layer is a smooth botanical layer having mentha, elderberry, honey, slippery elm, licorice and chamomile. The outer layer encapsulates an inner layer and provides a southing sensation as it dissolves. The inner layer provides long-lasting medicated relief and has aspirin, benzocaine and menthol. Extending from the head of the pop is a handle. The handle has a curved ergonomic shape designed for easy holding. The pop is used to lesson symptoms of a cold, including cough and sore throat. In this example, a subject places the pop in their mouth to receive the health benefits. The pop can also be stirred in a cup of liquid and consumed to receive the health benefits.

Example 6: Outside/Inside Cold Lozenge

In this example, a lozenge comprises an outer layer and an inner layer. The outer layer is a smooth botanical layer having mentha, elderberry, honey, slippery elm, licorice and chamomile. The outer layer encapsulates an inner layer soothes the mouth and throat as it dissolves. The inner layer delivers long-lasting medicated relief and has aspirin, benzocaine and menthol. The lozenge, when placed in a subject's mouth, lessens symptoms of a cold, including cough and sore throat.

Example 7: Sore Throat Pop

A pop has an outer layer and an inner layer at the head of the pop. The head of the pop has a smooth rectangular shape. The outer layer is a smooth botanical layer having menthol, slippery elm, juniper, elderberry and honey. The outer layer encapsulates an inner layer and delivers a soothing sensation as it dissolves in a subject's mouth. The inner layer delivers long-lasting medicate relief and has glycerin and dextromethorphan HBr. Extending from the head of the pop is a handle. The handle has a curved ergonomic shape designed for easy holding. The pop, when placed in a subject's mouth, ameliorates the presence of a sore throat.

Example 8: Cough and Cold Pop

A pop has an outer layer and an inner layer at the head of the pop. The head of the pop has a smooth oval shape. The outer layer is a smooth botanical layer having menthol, lemon balm, and peppermint. The outer layer encapsulates an inner layer and delivers a soothing sensation as it dissolves in a subject's mouth. The inner layer delivers long-lasting medicate relief and has diphenhydramine HCL and acetaminophen. Extending from the head of the pop is a handle. The handle has a curved ergonomic shape designed for easy holding. The pop, when placed in a subject's mouth, ameliorates the presence of a cough and cold.

Example 9: Outside/Inside Multi-Symptom Cold Relief Pop

A pop has an outer layer and an inner layer at the head of the pop. The head of the pop has a smooth circular shape. The outer layer is a smooth botanical layer having menthol, slippery elm, linden mallow and honey. The outer layer encapsulates an inner layer and delivers a soothing sensation as it dissolves in a subject's mouth. The inner layer delivers long-lasting medicate relief and has acetaminophen, chlorpheniramine maleate, dextromethorphan HBr, and phenylephrine HCL. Extending from the head of the pop is a handle. The handle has a curved ergonomic shape designed for easy holding. The pop, when placed in a subject's mouth, provides multi-symptom cold relief.

Example 10: Outside/Inside Multi-Symptom Relief Pop

A pop has an outer and an inner layer at the head of the pop. The head of the pop has a smooth circular shape. The outer layer is a smooth botanical layer having one or more ingredients for pain relief (Thyme, Echinacea, Horehound, Ginger, Spilanthes, Propolis, White Willow Bark, Cayenne, Sage), and one or more botanical ingredients for anti-inflammation (Marshmallow powder, Turmeric (Curcumin), Ginger, Thyme, White Willow Bark, Cayenne, Andographis, Propolis, Pelargonium Sidoides, Cinnamon powder), anti-microbial/anti-bacterial (Lavender, Thyme, Ginger Goldenseal, Echinacea, Spilanthes, Elderberry, Cayenne, Sage, Barberry, Propolis, Cinnamon powder), soothing/lubrication (Marshmallow powder, Licorice, Slippery Elm, Cinnamon powder, Pectin, Glycerin, Chamomile), or immune-boosting (Echinacea, Elderberry, Astragalus, Elderberry, Propolis) purposes. The outer layer encapsulates an inner layer dissolves first in a subject's mouth. The inner layer dissolves second and has one or more ingredients for pain relief (Aspirin, Naproxen, Ibuprofen, Acetaminophen, Menthol, Benzocaine, Lidocaine, Dyclonine, Hexylresorcinol, Menthol, Camphor), or anti-inflammation (Aspirin, Naproxen, Ibuprofen, Acetaminophen, Menthol, Ketoprofen) purposes. The handle has a curved ergonomic shape designed for easy holding. The pop, when placed in a subject's mouth, provides multi-symptom cold relief. It is understood that, depending on the desired properties, ingredients included can be altered in terms which are included and amount in order to focus on any particular symptom.

Example 11: Synergistic Relief Pop

A pop has an outer and an inner layer at the head of the pop. The head of the pop has a smooth circular shape. The outer layer is a smooth layer including a botanical ingredient selected from ingredients disclosed herein. The outer layer encapsulates an inner layer dissolves first in a subject's mouth. The inner layer dissolves second and has ingredients for medicated pain relief selected from ingredients disclosed herein. The handle has a curved ergonomic shape designed for easy holding. The pop, when placed in a subject's mouth, provides multi-symptom cold relief. The mix of ingredients provides a synergistic effect such that a lesser amount of the active pharmaceutical ingredient is required for a beneficial result as compared to using the active pharmaceutical ingredient without the botanical ingredient. It is understood that, depending on the desired properties, ingredients included can be altered in terms which are included and amount in order to focus on any particular symptom.

Example 12: Blended Lozenge for Sore Throat Relief

A lozenge in the shape of a sphere comprises a main layer that forms the outside of the sphere and also fills the interior of the sphere, except for pockets formed by smaller enclosed microstructures. The smaller microstructures are spheres as well and have the appearance of bubbles within the large sphere. The outer layer is a smooth layer having botanical ingredients, including mentha, elderberry, honey, slippery elm, licorice and chamomile. The outer/main layer encapsulates an inner layer/microstructures and soothes the mouth and throat as it dissolves. The inner bubbles deliver long-lasting medicated relief and include active pharmaceutical ingredients of aspirin, benzocaine and menthol. The lozenge, when placed in a subject's mouth, lessens symptoms of a sore throat. In additional examples, the ingredients can be swapped to be in opposite layers as described in this example or they can co-exist in the same layer. In additional examples, a handle can be inserted into the lozenge to form a "pop." In some instances, the sphere is dropped in fluid, such as a tea, to form a beverage in which the ingredients in the sphere dissolve.

Example 13: Beverage for Indigestion Relief

A beverage for relief from indigestion has a mixture of ingredients that, when consumed, provide relief for indigestion. Botanical ingredients for the mixture include: ginger, lemon balm, meadowsweet, slipper elm, marshmallow, catnip, rhubarb, licorice, mallow, gamma-oryzanol, peppermint, chamomile, blessed thistle, clubmoss, celandine, Chilean sassafras, Pau D'Arco, bark, natrum muriaticum, sepia, carbo vegetabilis or capsicum. Active pharmaceutical ingredients for the mixture include: bismuth subsalicylate, calcium carbonate, simethicone, aspirin, sodium bicarbonate, magnesium hydroxide, aluminum hydroxide, ranitidine HCl, cimetidine, famotidine, omeprazole, esomeprazole, or lansoprazole.

Example 14: Beverage for Nausea Relief

A beverage for nausea relief has a mixture of botanical ingredients and active pharmaceutical ingredients for nausea relief. The combination of ingredients, when consumed, provides relief for nausea. Botanical ingredients for the beverage are catnip, ginger and peppermint. Active pharmaceutical ingredients for the beverage are: bismuth subsalicylate, phosphorylated sugars, dozylamine succinate, diphenyhydramine, meclizine, sodium citrate dihydrate, calcium carbonate, dextrose, levulose, and/or phosphoric acid.

Example 15: Beverage for Upset Stomach Relief

A beverage for upset stomach relief has a mixture of botanical ingredients and active pharmaceutical ingredients. The combination of ingredients, when consumed, provides upset stomach relief Botanical ingredients are: slippery elm, mallow root, organic aloe and chamomile. The active pharmaceutical ingredient is bismuth subsalicylate.

Example 16: Beverage for Diarrhea Relief

A beverage for diarrhea relief has a mixture of botanical ingredients and active pharmaceutical ingredients. The combination of ingredients, when consumed, provides relief for diarrhea. Botanical ingredients for combination are: rhubarb, *bacillus coagulans*, licorice, mallow, *saccharomyces boulardii*, and fig. Active pharmaceutical ingredients for combination are: bismuth subsalicylate, phosphorylated sugars, dozylamine succinate, diphenyhydramine, meclizine, sodium citrate dihydrate, calcium carbonate, dextrose, levulose, and/or phosphoric acid.

Example 17: Beverage for Diarrhea Relief

A beverage for diarrhea relief has a mixture of botanical ingredients and an active pharmaceutical ingredient. The combination of ingredients, when consumed, provides relief for diarrhea. Botanical ingredients are: *lactobacillus acidophilis*, lactose, and chicory root. The active pharmaceutical ingredient is loperamine HCl.

Example 18: Beverage for Multi-Symptom Digestive Relief

A beverage for multi-symptom relief from indigestion has a mixture of botanical ingredients and active pharmaceutical ingredients. The combination of ingredients, when consumed, provides relief for multiple symptoms associated with digestive illness. Botanical ingredients for combination include: ginger, lemon balm, meadowsweet, slipper elm, marshmallow, catnip, rhubarb, licorice, ginger, mallow, gamma-oryzanol, peppermint, chamomile, blessed thistle, clubmoss, celandine, Chilean sassafras, Pau D'Arco, bark, natrum muriaticum, sepia, carbo vegetabilis, capsicum, rhubarb, *bacillus coagulans, saccharomyces boulardii, lactobacillus acidophilis*, lactose, chicory root and fig. Active pharmaceutical ingredients for combination include: bismuth subsalicylate, calcium carbonate, simethicone, aspirin, sodium bicarbonate, magnesium hydroxide, aluminum hydroxide, ranitidine HCl, cimetidine, famotidine, omeprazole, esomeprazole, lansoprazole, phosphorylated sugars, dozylamine succinate, diphenyhydramine, meclizine, sodium citrate dihydrate, calcium carbonate, dextrose, levulose, loperaminde HCl or phosphoric acid. It is understood that, depending on the desired properties, ingredients included can be altered in terms which are included and amount in order to focus on any particular symptom.

Example 19: Synergistic Beverage for Multi-Symptom Digestive Relief

A beverage for multi-symptom relief from indigestion has a mixture of botanical ingredients and active pharmaceutical ingredients. The combination of ingredients, when consumed, provides relief for multiple symptoms associated with digestive illness. The mix of ingredients provides a synergistic effect such that a lesser amount of the active pharmaceutical ingredient is required for a beneficial result as compared to using active pharmaceutical ingredients without the botanical ingredient. It is understood that, depending on the desired properties, ingredients included can be altered in terms which are included and amount in order to focus on any particular symptom.

Example 20: Beverage for Multi-Symptom Digestive Relief

A beverage for multi-symptom relief from indigestion has a mixture of at least one botanical ingredient and at least one active pharmaceutical ingredient. The combination of ingredients, when consumed, provides relief for multiple symptoms associated with digestive illness. The ingredients are located in a liquid and the liquid is encapsulated by a container with a removable opening on the upper surface, i.e. a soda can. The can contains a single dose which is sufficient to provide digestive relief for multiple symptoms associated with a digestive illness. The beverage is stable at room temperature. The can is ergonomically shaped such that it is conveniently shaped to be held by a hand.

Botanical ingredients for combination include: ginger, lemon balm, meadowsweet, slipper elm, marshmallow, catnip, rhubarb, licorice, ginger, mallow, gamma-oryzanol, peppermint, chamomile, blessed thistle, clubmoss, celandine, Chilean sassafras, Pau D'Arco, bark, natrum muriaticum, sepia, carbo vegetabilis, capsicum, rhubarb, *bacillus coagulans, saccharomyces boulardii, lactobacillus acidophilis*, lactose, chicory root and/or fig. Active pharmaceutical ingredients for combination include: bismuth subsalicylate, calcium carbonate, simethicone, aspirin, sodium bicarbonate, magnesium hydroxide, aluminum hydroxide, ranitidine HCl, cimetidine, famotidine, omeprazole, esomeprazole, lansoprazole, phosphorylated sugars, dozylamine succinate, diphenyhydramine, meclizine, sodium citrate dihydrate, calcium carbonate, dextrose, levulose, loperaminde HCl or phosphoric acid. It is understood that, depending on the desired properties, ingredients included can be altered in terms which are included and amount in order to focus on any particular symptom.

While the above is a complete description of various embodiments, any of a number of alternatives, modifications, and equivalents may be used in alternative embodiments. Therefore, the above description should not be taken as limiting the scope of the invention as it is defined by the appended claims.

What is claimed is:

1. A composition comprising:
a plurality of active pharmaceutical ingredients, wherein the plurality of active pharmaceutical ingredients comprises (i) calcium carbonate and simethicone or (ii) bismuth subsalicylate and simethicone; and
a plurality of botanical ingredients, wherein the plurality of botanical ingredients comprises five of the following: honey, chamomile, meadowsweet, turmeric, catnip, or lemon, wherein the plurality of active pharmaceutical ingredients and the plurality of botanical ingredients are present in a ratio by weight of 1:5 to 1:30, and wherein the composition is in a liquid dosage form.

2. The composition of claim 1, wherein the plurality of botanical ingredients consists of honey, chamomile, meadowsweet, lemon, and turmeric.

3. The composition of claim 1, wherein the catnip is catnip glycerin.

4. The composition of claim 1, wherein the lemon is lemon balm or lemon oil.

5. The composition of claim 1, wherein the chamomile is chamomile flower.

6. The composition of claim 1, wherein the meadowsweet is meadowsweet powder.

7. The composition of claim 1, wherein the plurality of botanical ingredients further comprises oats, marshmallow powder, cinnamon, or ginger.

8. The composition of claim 7, wherein the plurality of botanical ingredients consists of honey, oats, catnip, chamomile, marshmallow powder, meadowsweet, ginger, and turmeric.

9. The composition of claim 7, wherein the cinnamon is cinnamon powder, cinnamon tincture, or cinnamon oil.

10. The composition of claim 7, wherein the ginger is ginger power.

11. The composition of claim 1, wherein the plurality of active pharmaceutical ingredients further comprises alumina powder, calcium gluconate, calcium polycarbophil, carboxymethylcellulose sodium, charcoal, homatropine methylbromide, hyocyamine sulfate, kaolin, *lactobacillus* acidophilic, *lactobacillus bulgaricus*, loperamine HCl, opium, paregoric, pectin, phenyl salicylate, psyllium husk, polycarbophil, potassium carbonate, scopolamine hydrobromide, sodium carboxymethylcellulose, zinc phenolsulfonate, dimenhydrinate, meclizine hydrochloride, glutamic acid hydrochloride, acetaminophen, aluminum hydroxide, aspirin, caffeine, fructose, magnesium carbonate, magnesium trisilicate, sodium citrate, or sodium acetylsalicylate.

12. The composition of claim 1, wherein the plurality of active pharmaceutical ingredients and the plurality of botanical ingredients are present in a ratio by weight of 1:5 to 1:20.

13. The composition of claim 1, wherein the plurality of active pharmaceutical ingredients and the plurality of botanical ingredients are present in a ratio by weight of 1:5 to 1:11.

14. The composition of claim 1, wherein the plurality of active pharmaceutical ingredients and the plurality of botanical ingredients are present in a ratio by weight of about 1:7.5.

15. The composition of claim 1, further comprising a microstructure which comprises: the plurality of botanical ingredients, or the plurality of active pharmaceutical ingredients.

16. The composition of claim 1, wherein the liquid dosage form is carbonated or creamy.

17. The composition of claim 1, wherein the plurality of active pharmaceutical ingredients is present in an amount of 1100 mg to 2200 mg.

18. The composition of claim 1, wherein the plurality of botanical ingredients is present in an amount of 12000 mg to 13000 mg.

19. The composition of claim 1, wherein the plurality of active pharmaceutical ingredients is present in an amount of 1100 mg to 2200 mg, and wherein the plurality of botanical ingredients is present in an amount of 12000 mg to 13000 mg.

20. The composition of claim 1, wherein the plurality of active pharmaceutical ingredients is present in an amount of about 1625 mg, and wherein the plurality of botanical ingredients is present in an amount of about 12255 or about 12700 mg.

* * * * *